(12) United States Patent
Berniac et al.

(10) Patent No.: US 7,858,601 B2
(45) Date of Patent: Dec. 28, 2010

(54) 4-SUBSTITUTED TETRACYCLINES AND METHODS OF USE THEREOF

(75) Inventors: Joel Berniac, Stoneham, MA (US);
Beena Bhatia, Mansfield, MA (US);
Mark Grier, Watertown, MA (US);
Mark L. Nelson, Norfolk, MA (US);
Jingwen Pan, North Grafton, MA (US)

(73) Assignee: Paratek Pharmaceuticals, Inc., Boston, MA (US)

( * ) Notice: Subject to any disclaimer, the term of this patent is extended or adjusted under 35 U.S.C. 154(b) by 1133 days.

(21) Appl. No.: 11/258,613

(22) Filed: Oct. 25, 2005

(65) Prior Publication Data

US 2006/0166944 A1 Jul. 27, 2006

Related U.S. Application Data

(60) Provisional application No. 60/622,027, filed on Oct. 25, 2004, provisional application No. 60/673,827, filed on Apr. 21, 2005.

(51) Int. Cl.
*A61K 31/65* (2006.01)
*C07C 237/26* (2006.01)

(52) U.S. Cl. .................. 514/152; 552/205
(58) Field of Classification Search .......... 552/205; 514/152
See application file for complete search history.

(56) References Cited

U.S. PATENT DOCUMENTS

| | | | |
|---|---|---|---|
| 2,980,584 A | 4/1961 | Hammer | 167/65 |
| 2,990,331 A | 6/1961 | Neumann et al. | 167/65 |
| 2,997,471 A | 8/1961 | Cheney et al. | 260/247.2 |
| 3,047,617 A | 7/1962 | Blackwood et al. | 260/490 |
| 3,062,717 A | 11/1962 | Hammer | 167/65 |
| 3,159,675 A * | 12/1964 | Esse et al. | 552/203 |
| 3,165,531 A | 1/1965 | Blackwood et al. | 260/330.5 |
| 3,183,267 A | 5/1965 | Blackwood et al. | 260/559 |
| 3,345,370 A * | 10/1967 | Esse et al. | 544/154 |
| 3,454,697 A | 7/1969 | Joyner et al. | 424/227 |
| 3,557,280 A | 1/1971 | Weber et al. | 424/80 |
| 3,609,188 A | 9/1971 | Esse et al. | |
| 3,622,627 A | 11/1971 | Blackwood et al. | 260/559 |
| 3,674,859 A | 7/1972 | Beutel et al. | 424/80 |
| 3,824,285 A | 7/1974 | Blackwood et al. | 260/559 |
| 3,957,980 A | 5/1976 | Noseworthy | 424/227 |
| 4,018,889 A | 4/1977 | Armstrong | 424/80 |
| 4,024,272 A | 5/1977 | Rogalski et al. | 424/275 |
| 4,126,680 A | 11/1978 | Armstrong | 424/80 |
| 5,498,699 A | 3/1996 | Djokic et al. | |
| 6,043,231 A | 3/2000 | Pruzanski et al. | 514/152 |
| 6,500,812 B2 | 12/2002 | Nelson et al. | |
| 6,506,740 B1 * | 1/2003 | Ashley et al. | 514/152 |
| 6,613,756 B2 | 9/2003 | Duncan et al. | |
| 6,617,318 B1 | 9/2003 | Nelson et al. | |
| 6,624,168 B2 | 9/2003 | Nelson et al. | |
| 6,638,922 B2 | 10/2003 | Ashley et al. | |
| 6,642,270 B2 | 11/2003 | Nelson et al. | |
| 6,683,068 B2 | 1/2004 | Nelson et al. | |
| 6,818,634 B2 | 11/2004 | Nelson et al. | |
| 6,818,635 B2 | 11/2004 | Nelson et al. | |
| 6,833,365 B2 | 12/2004 | Levy et al. | |
| 6,841,546 B2 | 1/2005 | Draper et al. | |
| 6,846,939 B2 | 1/2005 | Nelson et al. | |
| 6,849,615 B2 | 2/2005 | Nelson et al. | |
| 6,894,036 B2 | 5/2005 | Ashley et al. | |
| 6,946,453 B2 | 9/2005 | Ashley et al. | |
| 7,001,918 B2 | 2/2006 | Huss et al. | |
| 7,045,507 B2 | 5/2006 | Draper et al. | |
| 7,056,902 B2 | 6/2006 | Nelson et al. | |
| 7,067,681 B2 | 6/2006 | Nelson et al. | |
| 7,075,582 B2 | 7/2006 | Alekshun et al. | |
| 2002/0022608 A1 | 2/2002 | Duncan et al. | |
| 2002/0123637 A1 | 9/2002 | Levy et al. | |
| 2002/0128237 A1 | 9/2002 | Nelson et al. | |
| 2002/0128238 A1 | 9/2002 | Nelson et al. | |
| 2002/0132798 A1 | 9/2002 | Nelson et al. | |
| 2002/0160987 A1 | 10/2002 | Ashley et al. | |
| 2003/0055025 A1 | 3/2003 | Nelson et al. | |
| 2003/0125348 A1 | 7/2003 | Nelson et al. | |
| 2003/0166952 A1 | 9/2003 | Nelson et al. | |
| 2003/0195174 A1 | 10/2003 | Ashley et al. | |

(Continued)

FOREIGN PATENT DOCUMENTS

| | | |
|---|---|---|
| BE | 650353 | 11/1965 |
| CN | 1811454 | 2/2006 |
| NL | 6411182 | 4/1965 |
| WO | WO-03/005971 A2 | 1/2003 |
| WO | WO-2004/064728 A2 | 8/2004 |
| WO | WO 2005/009943 A2 | 2/2005 |
| WO | WO 2005/056538 A1 | 6/2005 |
| WO | WO 2006/047671 A2 | 5/2006 |
| WO | WO 2008/079339 A2 | 7/2008 |

OTHER PUBLICATIONS

Charest et al., "A convergent enantioselective route to structurally diverse 6-deoxytetracycline antibiotics", *Science*, 308:395-398 (2005).
Von Wittenau et al., "Proton magnetic resonance spectra of tetracyclines", *J. Org. Chem.*, 31:613-615 (1966).
Nelson et al., "Molecular requirements for the inhibition of the tetracycline antiport protein and the effect of potent inhibitors on the growth of tetracycline-resistant bacteria", *J. Med. Chem.*, 37:1355-1361 (1994).

(Continued)

*Primary Examiner*—Barbara P Badio
(74) *Attorney, Agent, or Firm*—Mintz Levin Cohn Ferris Glovsky and Popeo, P.C.; Ivor R. Elrifi; Heidi A. Erlacher

(57) ABSTRACT

The present invention pertains, at least in part, to novel substituted tetracycline compounds. These tetracycline compounds can be used to treat numerous tetracycline compound-responsive states, such as bacterial infections and neoplasms, as well as other known applications for tetracycline compounds such as blocking tetracycline efflux and modulation of gene expression.

10 Claims, No Drawings

U.S. PATENT DOCUMENTS

| | | |
|---|---|---|
| 2004/0002481 A1 | 1/2004 | Ashley et al. |
| 2004/0048835 A1 | 3/2004 | Nelson et al. |
| 2004/0063674 A1 | 4/2004 | Levy et al. |
| 2004/0067912 A1 | 4/2004 | Hlavka et al. |
| 2004/0092490 A1 | 5/2004 | Draper et al. |
| 2004/0138183 A1 | 7/2004 | Nelson et al. |
| 2004/0152674 A1 | 8/2004 | Levy et al. |
| 2004/0176334 A1 | 9/2004 | Nelson et al. |
| 2004/0214800 A1 | 10/2004 | Levy et al. |
| 2004/0214801 A1 | 10/2004 | Nelson et al. |
| 2004/0242548 A1 | 12/2004 | Draper et al. |
| 2004/0266740 A1 | 12/2004 | Huss et al. |
| 2005/0020545 A1 | 1/2005 | Draper et al. |
| 2005/0026875 A1 | 2/2005 | Nelson et al. |
| 2005/0026876 A1 | 2/2005 | Nelson et al. |
| 2005/0038002 A1 | 2/2005 | Nelson et al. |
| 2005/0070510 A1 | 3/2005 | Draper et al. |
| 2005/0119235 A1 | 6/2005 | Nelson et al. |
| 2005/0137174 A1 | 6/2005 | Ohemeng et al. |
| 2005/0143352 A1 | 6/2005 | Nelson et al. |
| 2005/0143353 A1 | 6/2005 | Nelson et al. |
| 2005/0148551 A1 | 7/2005 | Nelson et al. |
| 2005/0187198 A1 | 8/2005 | Nelson et al. |
| 2005/0215532 A1 | 9/2005 | Levy et al. |
| 2005/0245491 A9 | 11/2005 | Hlavka et al. |
| 2005/0250744 A1 | 11/2005 | Levy et al. |
| 2005/0267079 A1 | 12/2005 | Hlavka et al. |
| 2005/0282787 A1 | 12/2005 | Myers et al. |
| 2005/0288262 A1 | 12/2005 | Bandarage et al. |
| 2006/0003971 A1 | 1/2006 | Nelson |
| 2006/0008463 A1 | 1/2006 | Itoh et al. |
| 2006/0008467 A1 | 1/2006 | Haynes et al. |
| 2006/0008933 A1 | 1/2006 | Muller et al. |
| 2006/0014876 A1 | 1/2006 | Bushelman et al. |
| 2006/0016694 A1 | 1/2006 | Tanaka et al. |
| 2006/0089336 A1 | 4/2006 | Nelson et al. |

OTHER PUBLICATIONS

Martin et al., "Totalsynthese von d, 1-7-chlor-6-desoxytetracyclinen und d, 1-7-chlor-6-desmethyl-6-desoxytetracyclinen der naturlichen, der 5a-epi- und der 6-epi-reihe", *Tetrahedron Lett.*, 36:3513-3516 (1973).
Barton et al., "Reaction of tetracycline hydrochloride with N-chlorosuccinimide: X-ray crystal structure of the major product", *J.C.S. Chem. Comm.*, 21:790-791 (1977).
Bhattacharyya et al., "Studies on hydrofluorene derivatives. Part II. Synthesis of 1,1a,1b,2,3,4,4a,5,6,6a-decahydro-1a-methyl-3-oxochyrsofluorene", *J. Ind. Chem. Soc.*, 41(7):479-495 (1964).
Blackwood et al., "Novel C-4 modified tetracycline derivatives", *J. Am. Chem. Soc.*, 86(13):2736-2737 (1964).
Blackwood et al., "Some transformations of tetracycline at the 4-position", *Can. J Chem.*, 43(5):1382-1388 (1965).
Davies et al., "Photochemical oxidation of tetracycline in aqueous solution",*J. Chem. Soc. Perkin Trans. 2:Phys. Org. Chem.*, 3:369-375 (1979).
Deyrup et al., "Nucleophilic displacements on three-membered rings", *J. Am. Chem. Soc.*, 87(20):4538-4545 (1965).
Esse et al., "Tetracycloxides. I. A new class of tetracycline derivatives",*J. Am. Chem. Soc.*, 86(18):3874-3875 (1964).
Gurevich et al., "Action of tetracycline analogs on protein and nucleic acid biosyntheses in *Escherichia coli*", *Biokhimiya*, in Russian, English Abstract only, 39(2):421-425 (1974).
Gurevich et al., "Tetracyclines. LIII. Reactions of tetracycloxides and N-demethyltetracyclines". *Khimiya Prirodnykh Soedinenii*, in Russian, English Abstract only, 6(2):247-251 (1970).
Hlavka et al., "4-hydroxy-6-methylpretetramid-synthesis via quaternary tetracyclines",*J. Am. Chem. Soc*, 87(8):1795-1797 (1965).
Hlavka et al., "4-hydroxypretetramids",*J. Am. Chem. Soc.*, 90(4):1034-1037 (1968).
Huang et al., "Synthesis of tetracycline analogs and their bone affinities",*Chinese Chem. Lett.*, 19(1):19-22 (2008).
Rauen et al., "Complex formation and alkylation reaction of 2.3. 4tris(aziridinyl)-1,4-benzoquinone with 2,3-dimercaptopropan-1-ol", *Arzneimittel-Forschung*, in German, English Abstract only, 15(8):892-893 (1965).
Williams et al., "The characterization of unsaturated compounds by means of acycyclone", *Makromolekulare Chemie*, 82:281-283 (1965).
CAPLUS Accession No. 1978:169817, Barton, Derek et al. "Reaction of tetracycline hydrochloride with N-chlorosuccinimide: x-ray crystal structure of the major product," *Journal of the Chemical Society, Chemical Communications*, vol. 21:790-791 (1977), Abstract only.
El-Astal, Z., "Bacterial Pathogens and their Antimicrobial Susceptibility in Gaza Strip, Palestine," *Pak. J. Med. Sci.*, vol. 20(4):365-370 (2004).
CAPLUS Accession No. 1964:492220, Esse, Robert C. et al, "Tetracycloxides. I. A new class of tetracycline derivatives," *Journal of the American Chemical Society*, vol. 86(18):3874-3875 (1964), Abstract only.
Prof. Dr. Jürgen Falbe und Prof. Dr. Manfred REgitz: "Römpp Chemie Lexikon" 1992, Georg Thieme Verlag, Stuttgart, pp. 4523-4524.
Hryniewicz, Katarzyna et al, "Antibiotic susceptibility of bacterial strains isolated from urinary tract infections in Poland," *Journal of Antimicrobial Chemotherapy*, vol. 47:773-780 (2001).
Testa, Raymond T. et al, "In Vitro and In Vivo Antibacterial Activities of the Glycylcyclines, a New Class of Semisynthetic Tetracyclines," *Antimicrobial Agents and Chemotherapy*, vol. 37(11):2270-2277 (1993).
Communication Relating to the Results of the Partial Search enclosed with Invitation to Pay Additional Fees for Applciation No. PCT/US2005/038733, dated Mar. 24, 2006.
US 6,897,204, 05/2005, Hlavka et al. (withdrawn)

* cited by examiner

4-SUBSTITUTED TETRACYCLINES AND METHODS OF USE THEREOF

RELATED APPLICATIONS

This application claims priority to U.S. Provisional Patent Application No. 60/622,027, filed on Oct. 25, 2004 and U.S. Provisional Patent Application No. 60/673,827, filed on Apr. 21, 2005, the contents of each of which are incorporated herein by reference.

BACKGROUND OF THE INVENTION

The development of the tetracycline antibiotics was the direct result of a systematic screening of soil specimens collected from many parts of the world for evidence of microorganisms capable of producing bacteriocidal and/or bacteriostatic compositions. The first of these novel compounds was introduced in 1948 under the name chlortetracycline. Two years later, oxytetracycline became available. The elucidation of the chemical structure of these compounds confirmed their similarity and furnished the analytical basis for the production of a third member of this group in 1952, tetracycline. A new family of tetracycline compounds, without the ring-attached methyl group present in earlier tetracyclines, was prepared in 1957 and became publicly available in 1967; and minocycline was in use by 1972.

Recently, research efforts have focused on developing new tetracycline antibiotic compositions effective under varying therapeutic conditions and routes of administration. New tetracycline analogues have also been investigated which may prove to be equal to or more effective than the originally introduced tetracycline compounds. Examples include U.S. Pat. Nos. 2,980,584; 2,990,331; 3,062,717; 3,165,531; 3,454,697; 3,557,280; 3,674,859; 3,957,980; 4,018,889; 4,024,272; and 4,126,680. These patents are representative of the range of pharmaceutically active tetracycline and tetracycline analogue compositions.

Historically, soon after their initial development and introduction, the tetracyclines were found to be highly effective pharmacologically against rickettsiae; a number of gram-positive and gram-negative bacteria; and the agents responsible for lymphogranuloma venereum, inclusion conjunctivitis, and psittacosis. Hence, tetracyclines became known as "broad spectrum" antibiotics. With the subsequent establishment of their in vitro antimicrobial activity, effectiveness in experimental infections, and pharmacological properties, the tetracyclines as a class rapidly became widely used for therapeutic purposes. However, this widespread use of tetracyclines for both major and minor illnesses and diseases led directly to the emergence of resistance to these antibiotics even among highly susceptible bacterial species both commensal and pathogenic (e.g., *pneumococci* and *Salmonella*). The rise of tetracycline-resistant organisms has resulted in a general decline in use of tetracyclines and tetracycline analogue compositions as antibiotics of choice.

SUMMARY OF THE INVENTION

In one embodiment, the invention includes tetracycline compounds of formula (I):

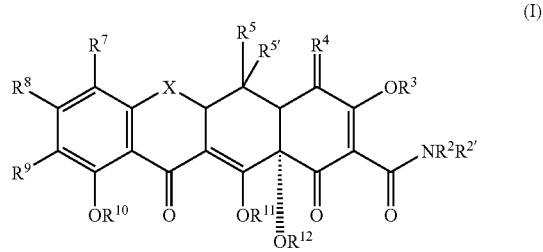

wherein:
- $R^{2'}$ and $R^2$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- $R^{10}$, $R^{11}$ and $R^{12}$ are each independently hydrogen, alkyl, aryl, benzyl, arylalkyl, or a pro-drug moiety;
- $R^3$ is hydroxyl, hydrogen, or a pro-drug moiety;
- $R^4$ is O or N—$OR^{4a}$;
- $R^{4a}$ is hydrogen, alkyl, alkenyl, alkynyl, or aryl;
- $R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
- $R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
- $R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}(NR^{7c})_{0-1}C(\!=\!W')WR^{7a}$;
- $R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}(NR^{8c})_{0-1}C(\!=\!E')ER^{8a}$;
- $R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —$(CH_2)_{0-3}(NR^{9c})_{0-1}CC(\!=\!Z')ZR^{9a}$;
- $R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- $R^{13}$ is hydrogen, hydroxy, alkyl, alkenyl, alkynyl, alkoxy, alkylthio, aryl, alkylsulfinyl, alkylsulfonyl, alkylamino, or an arylalkyl;
- E is $CR^{8d}R^{8e}$, S, $NR^{8b}$ or O;
- E' is O, $NR^{8f}$, or S;
- W is $CR^{7d}R^{7e}$, S, $NR^{7b}$ or O;
- W' is O, $NR^{7f}$, or S;
- X is $CHC(R^{13}Y'Y)$, $C\!=\!CR^{13}Y$, $CR^6R^6$, S, $NR^6$, or O;
- Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;
- P Z is $CR^{9d}R^{9e}$, S, $NR^{9b}$ or O;

Z' is O, S, or $NR^{9f}$ and pharmaceutically acceptable salts, esters and enantiomers thereof.

In another embodiment, the invention pertains, at least in part, to tetracycline compounds of formula (II):

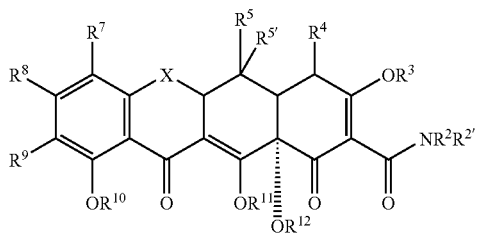

(II)

wherein:
- $R^{2'}$ and $R^2$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- $R^{10}$, $R^{11}$ and $R^{12}$ are each independently hydrogen, alkyl, aryl, benzyl, arylalkyl, or a pro-drug moiety;
- $R^3$ is hydroxyl, hydrogen, or a pro-drug moiety;
- $R^4$ is $NR^{4c}R^{4d}$;
- $R^{4c}$ and $R^{4d}$ are each independently hydrogen, sulfonyl, arylcarbonyl, arylaminocarbonyl, aryloxycarbonyl, alkylcarbonyl, alkylaminocarbonyl, alkyloxycarbonyl, acyl, alkyl, alkenyl, alkynyl, or aryl;
- $R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
- $R^6$ and $R^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
- $R^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(NR^{7c})_{0-1}C(=W')WR^{7a}$;
- $R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or $-(CH_2)_{0-3}(NR^{8c})_{0-1}C(=E')ER^{8a}$;
- $R^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or $-(CH_2)_{0-3}(R^{9c})_{0-1}C(=Z')ZR^{9a}$;
- $R^{7a}$, $R^{7b}$, $R^{7c}$, $R^{7d}$, $R^{7e}$, $R^{7f}$, $R^{8a}$, $R^{8b}$, $R^{8c}$, $R^{8d}$, $R^{8e}$, $R^{8f}$, $R^{9a}$, $R^{9b}$, $R^{9c}$, $R^{9d}$, $R^{9e}$, and $R^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
- $R^{13}$ is hydrogen, hydroxy, alkyl, alkenyl, alkynyl, alkoxy, alkylthio, aryl, alkylsulfinyl, alkylsulfonyl, alkylamino, or an arylalkyl;
- E is $CR^{8d}R^{8e}$, S, $NR^{8b}$ or O;
- E' is O, $NR^{8f}$, or S;
- W is $CR^{7d}R^{7e}$, S, $NR^{7b}$ or O;
- W' is O, $NR^{7f}$, or S;
- X is $CHC(R^{13}Y'Y)$, $C=CR^{13}Y$, $CR^6R^6S$, $NR^6$, or O;
- Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;
- Z is $CR^{9d}R^{9e}$, S, $NR^{9b}$ or O;
- Z' is O, S, or $NR^{9f}$, and pharmaceutically acceptable salts, esters and enantiomers thereof.

In another further embodiment, the invention pertains, at least in part, to methods for treating subjects for tetracycline responsive states by administering to them an effective amount of a tetracycline compound of the invention, e.g., a compound of Formula I or II or a tetracycline compound otherwise described herein.

In another further embodiment, the invention pertains, at least in part, to to pharmaceutical compositions which comprise an effective amount of a tetracycline compound of the invention, e.g., a compound of Formula I or II or a tetracycline compound otherwise described herein, and a pharmaceutically acceptable carrier.

DETAILED DESCRIPTION OF THE INVENTION

The present invention pertains, at least in part, to novel substituted tetracycline compounds. These tetracycline compounds can be used to treat numerous tetracycline compound-responsive states, such as bacterial infections and neoplasms, as well as other known applications for minocycline and tetracycline compounds in general, such as blocking tetracycline efflux and modulation of gene expression.

The term "tetracycline compound" includes many compounds with a similar ring structure to tetracycline. Examples of tetracycline compounds include: chlortetracycline, oxytetracycline, demeclocycline, methacycline, sancycline, chelocardin, rolitetracycline, lymecycline, apicycline; clomocycline, guamecycline, meglucycline, mepylcycline, penimepicycline, pipacycline, etamocycline, penimocycline, etc. Other derivatives and analogues comprising a similar four ring structure are also included (See Rogalski, "Chemical Modifications of Tetracyclines," the entire contents of which are hereby incorporated herein by reference). Table 1 depicts tetracycline and several known other tetracycline derivatives.

TABLE 1

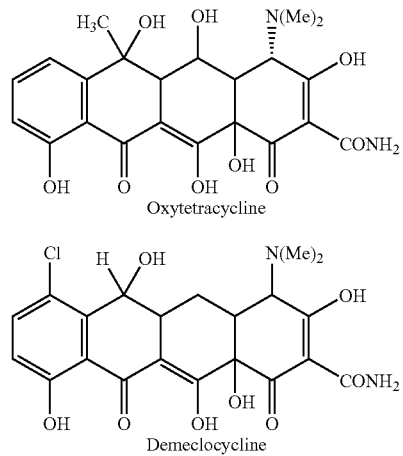

Oxytetracycline

Demeclocycline

TABLE 1-continued

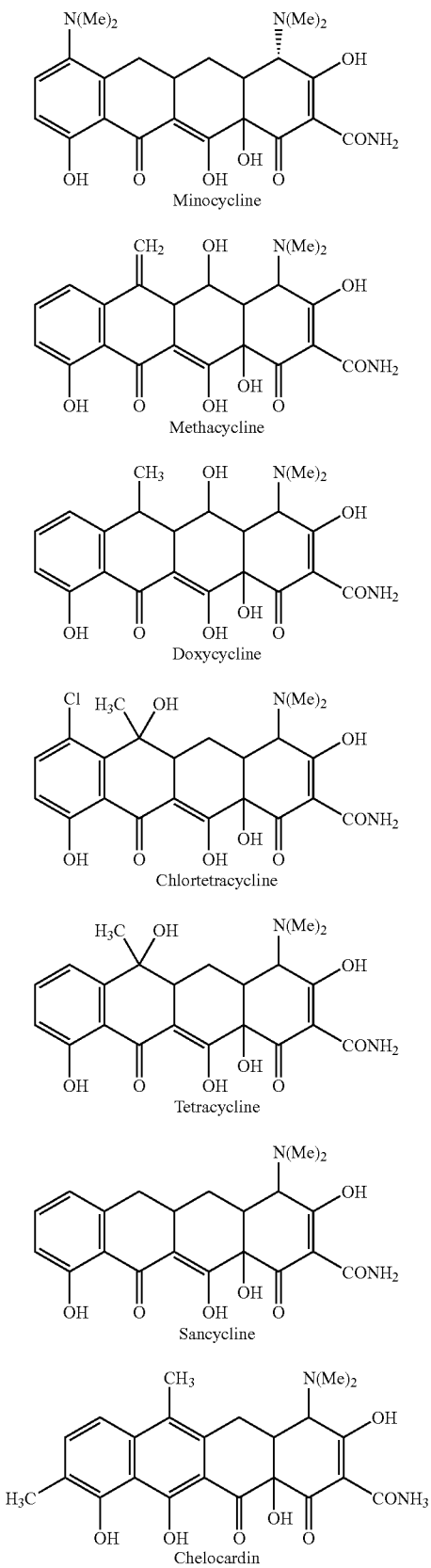

Other tetracycline compounds which may be modified using the methods of the invention include, but are not limited to, 6-demethyl-6-deoxy-4-dedimethylaminotetracycline; tetracyclino-pyrazole; 7-chloro-4-dedimethylaminotetracycline; 4-hydroxy-4-dedimethylaminotetracycline; 12α-deoxy-4-dedimethylaminotetracycline; 5-hydroxy-6α-deoxy-4-dedimethylaminotetracycline; 4-dedimethylamino-12α-deoxyanhydrotetracycline; 7-dimethylamino-6-demethyl-6-deoxy-4-dedimethylaminotetracycline; tetracyclinonitrile; 4-oxo-4-dedimethylaminotetracycline 4,6-hemiketal; 4-oxo-11a Cl-4-dedimethylaminotetracycline-4,6-hemiketal; 5a, 6-anhydro-4-hydrazon-4-dedimethylamino tetracycline; 4-hydroxyimino-4-dedimethylamino tetracyclines; 4-hydroxyimino-4-dedimethylamino 5a,6-anhydrotetracyclines; 4-amino-4-dedimethylamino-5a, 6 anhydrotetracycline; 4-methylamino-4-dedimethylamino tetracycline; 4-hydrazono-11a-chloro-6-deoxy-6-demethyl-6-methylene-4-dedimethylamino tetracycline; tetracycline quaternary ammonium compounds; anhydrotetracycline betaines; 4-hydroxy-6-methyl pretetramides; 4-keto tetracyclines; 5-keto tetracyclines; 5a, 11a dehydro tetracyclines; 11a Cl-6, 12 hemiketal tetracyclines; 11a Cl-6-methylene tetracyclines; 6,13 diol tetracyclines; 6-benzylthiomethylene tetracyclines; 7,11a-dichloro-6-fluoro-methyl-6-deoxy tetracyclines; 6-fluoro (α)-6-demethyl-6-deoxy tetracyclines; 6-fluoro (β)-6-demethyl-6-deoxy tetracyclines;6-α acetoxy-6-demethyl tetracyclines; 6-β acetoxy-6-demethyl tetracyclines; 7,13-epithiotetracyclines; oxytetracyclines; pyrazolotetracyclines; 11a halogens of tetracyclines; 12a formyl and other esters of tetracyclines; 5, 12a esters of tetracyclines; 10,12a-diesters of tetracyclines; isotetracycline; 12-a-deoxyanhydro tetracyclines; 6-demethyl-12a-deoxy-7-chloroanhydrotetracyclines; B-nortetracyclines; 7-methoxy-6-demethyl-6-deoxytetracyclines; 6-demethyl-6-deoxy-5a-epitetracyclines; 8-hydroxy-6-demethyl-6-deoxy tetracyclines; monardene; chromocycline; 5a methyl-6-demethyl-6-deoxy tetracyclines; 6-oxa tetracyclines, and 6 thia tetracyclines.

4-Substituted Tetracycline Compounds

In one embodiment, the invention includes tetracycline compounds of formula

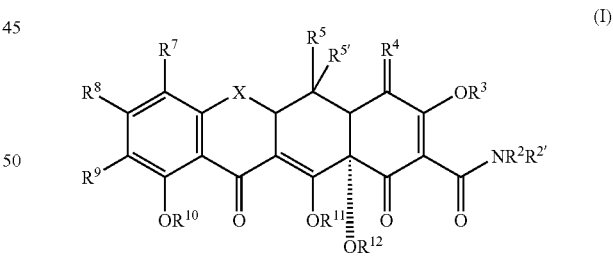

(I)

wherein:
R[2']and R[2] are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R[10], R[11] and R[12] are each independently hydrogen, alkyl, aryl, benzyl, arylalkyl, or a pro-drug moiety;

R[3] is hydroxyl, hydrogen, or a pro-drug moiety;

R[3'] is hydroxyl, hydrogen, or a pro-drug moiety;

R[4] is O or N—OR[4a];

R[4a] is hydrogen, alkyl, alkenyl, alkynyl, or aryl;

R⁵ and R⁵' are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;

R⁶ and R⁶' are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;

R⁷ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH₂)₀₋₃(NR⁷ᶜ)₀₋₁C(=W')WR⁷ᵃ;

R⁸ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —(CH₂)₀₋₃(NR⁸ᶜ)₀₋₁C(=E')ER⁸ᵃ;

R⁹ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH₂)₀₋₃(NR⁹ᶜ)₀₋₁C(=Z')ZR⁹ᵃ;

R⁷ᵃ, R⁷ᵇ, R⁷ᶜ, R⁷ᵈ, R⁷ᶠ, R⁸ᵃ, R⁸ᵇ, R⁸ᶜ, R⁸ᵈ, R⁸ᵉ, R⁸ᶠ, R⁹ᵃ, R⁹ᵇ, R⁹ᶜ, R⁹ᵈ, R⁹ᵉ, and R⁹ᶠ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;

R¹³ is hydrogen, hydroxy, alkyl, alkenyl, alkynyl, alkoxy, alkylthio, aryl, alkylsulfinyl, alkylsulfonyl, alkylamino, or an arylalkyl;

P E is CR⁸ᵈR⁸ᵉ, S, NR⁸ᵇ or O;

E' is O, NR⁸ᶠ, or S;

W is CR⁷ᵈR⁷ᵉ, S, NR⁷ᵇ or O;

W' is O, NR⁷ᶠ, or S;

X is CHC(R¹³Y'Y), C=CR¹³Y, CR⁶R⁶', S, NR⁶, or O;

Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;

Z is CR⁹ᵈR⁹ᵉ, S, NR⁹ᵇ or O;

Z' is O, S, or NR⁹ᶠ, and pharmaceutically acceptable salts, esters and enantiomers thereof.

In a further embodiment, R²', R³, R¹⁰, and R¹² are each hydrogen or a prodrug moiety; X is CR⁶R⁶'; R², R⁵, R⁵', R⁶, and R⁶' are each hydrogen.

Alternatively, R⁵ and R⁵' are hydrogen and X is CR⁶R⁶', wherein R⁶ is methyl and R⁶' is hydroxy. Alternatively, when R⁵ is hydroxyl; X is CR⁶R⁶'; R⁶ is methyl; and R⁵' and R⁶' are hydrogen. In yet another embodiment, X is CR⁶R⁶'; R⁵, R⁵', R⁶ and R⁶' are hydrogen atoms and R⁷ is dimethylamino.

In one embodiment, R⁹ is hydrogen. In another embodiment, R⁹ is substituted or unsubstituted aryl (e.g., phenyl or heteroaryl). In another embodiment, R⁹ is substituted or unsubstituted alkyl. In a further embodiment, R⁹ is aminoalkyl, e.g., aminomethyl (e.g., —CH₂—N⁹ⁿR⁹ᵐ, wherein R⁹ⁿ is hydrogen or a prodrug and R⁹ᵐ is hydrogen or lower alkyl).

In another embodiment, R⁷ is hydrogen. In yet another embodiment, R⁷ is substituted or unsubstituted aryl, e.g., phenyl or heteroaryl (e.g., pyridinyl, pyrrolyl, pyrazinyl, etc.). In another embodiment, R⁷ is substituted or unsubstituted amino (e.g., dimethylamino), nitro or halogen.

In a further embodiment, R⁴ is O. In another embodiment, R⁴ is N—OH.

In another further embodiment, the tetracycline compound is:

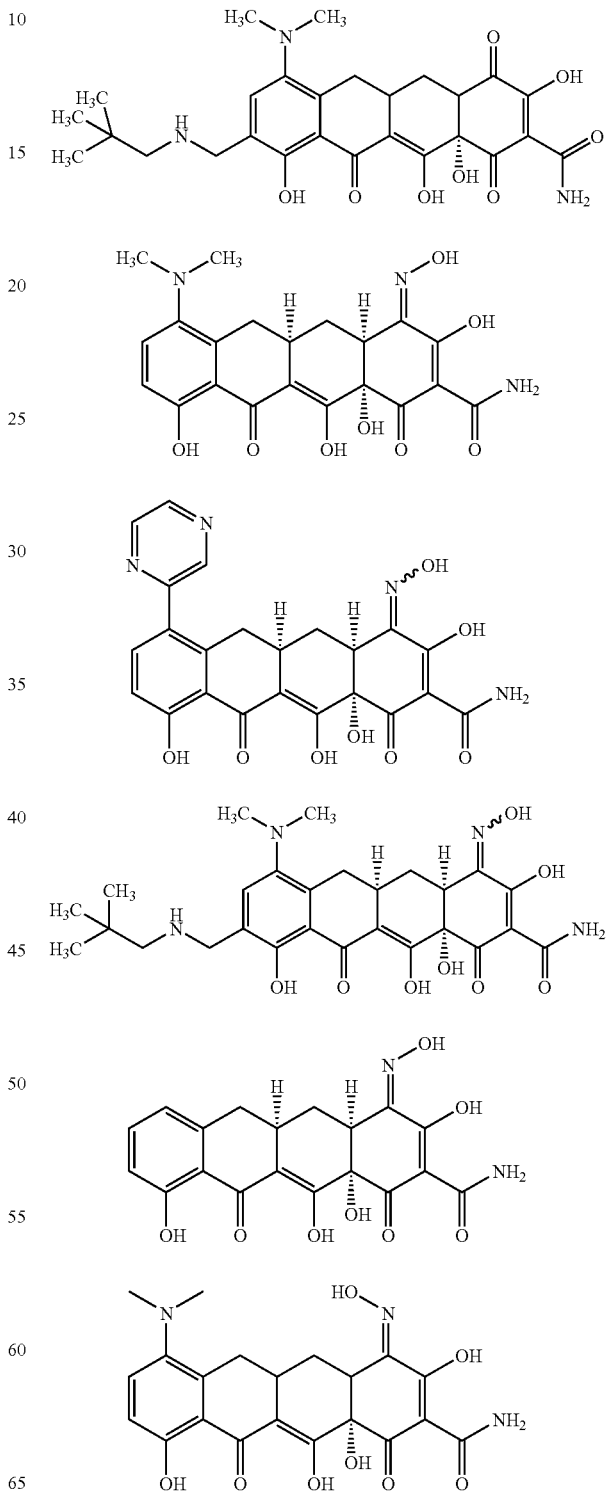

In a further embodiment, the invention pertains to compounds of the formula (II):

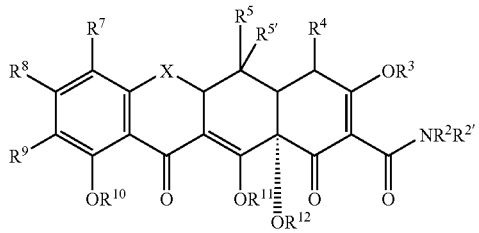

(II)

wherein:
R$^{2'}$ and R$^2$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^{10}$, R$^{11}$ and R$^{12}$ are each independently hydrogen, alkyl, aryl, benzyl, arylalkyl, or a pro-drug moiety;
R$^3$ is hydroxyl, hydrogen, or a pro-drug moiety;
R$^{3'}$ is hydroxyl, hydrogen, or a pro-drug moiety;
R$^4$ is NR$^{4c}$R$^{4d}$;
R$^{4c}$ and R$^{4d}$ are each independently hydrogen, sulfonyl, arylcarbonyl, arylaminocarbonyl, aryloxycarbonyl, alkylcarbonyl, alkylaminocarbonyl, alkyloxycarbonyl, acyl, alkyl, alkenyl, alkynyl, or aryl;
R$^5$ and R$^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
R$^6$ and R$^{6'}$ are each independently hydrogen, methylene, absent, hydroxyl, halogen, thiol, alkyl, alkenyl, alkynyl, aryl, alkoxy, alkylthio, alkylsulfinyl, alkylsulfonyl, alkylamino, or an arylalkyl;
R$^7$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH$_2$)$_{0-3}$(NR$^{7c}$)$_{0-1}$C(=W')WR$^{7a}$;
R$^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —(CH$_2$)$_{0-3}$(NR$^{8c}$)$_{0-1}$C(=E')ER$^{8a}$;
R$^9$ is hydrogen, hydroxyl, halogen, thiol, nitro, alkyl, alkenyl, alkynyl, aryl, alkoxy, alkylthio, alkylsulfinyl, alkylsulfonyl, arylalkyl, amino, arylalkenyl, arylalkynyl, acyl, aminoalkyl, heterocyclic, thionitroso, or —(CH$_2$)$_{0-3}$(NR$^{9c}$)$_{0-1}$C(=Z')ZR$^{9a}$;
R$^{7a}$, R$^{7b}$, R$^{7c}$, R$^{7d}$, R$^{7e}$, R$^{7f}$, R$^{8a}$, R$^{8b}$, R$^{8c}$, R$^{8d}$, R$^{8e}$, R$^{8f}$, R$^{9a}$, R$^{9b}$, R$^{9c}$, R$^{9d}$, R$^{9e}$, and R$^{9f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
R$^{13}$ is hydrogen, hydroxy, alkyl, alkenyl, alkynyl, alkoxy, alkylthio, aryl, alkylsulfinyl, alkylsulfonyl, alkylamino, or an arylalkyl;
E is CR$^{8d}$R$^{8e}$, S, NR$^{8b}$ or O;
E' is O, NR$^{8f}$ for S;
W is CR$^{7d}$R$^{7e}$, S, NR$^{7b}$ or O;
W' is O, NR$^{7f}$, or S;
X is CHC(R$^{13}$Y'Y), C=CR$^{13}$Y, CR$^6$R$^6$, S, NR$^6$, or O;
Y' and Y are each independently hydrogen, halogen, hydroxyl, cyano, sulfhydryl, amino, alkyl, alkenyl, alkynyl, alkoxy, alkylthio, alkylsulfinyl, alkylsulfonyl, alkylamino, or an arylalkyl;
Z is CR$^{9d}$R$^{9e}$, S, NR$^{9b}$ or O;
Z' is O, S, or NR$^{9f}$, and pharmaceutically acceptable salts, esters and enantiomers thereof.

In a further embodiment, R$^{2'}$, R$^3$, R$^{10}$, R$^{11}$, and R$^{12}$ are each hydrogen or a prodrug moiety; X is CR$^6$R$^{6'}$; and R$^2$, R$^5$, R$^{5'}$, R$^6$, and R$^{6'}$ are each hydrogen.

Alternatively, R$^5$ and R$^{5'}$ are hydrogen and X is CR$^6$R$^{6'}$, wherein R$^6$ is methyl and R$^{6'}$ is hydroxy. Alternatively, when R$^5$ is hydroxyl; X is CR$^6$R$^{6'}$; R$^6$ is methyl; and R$^{5'}$ and R$^{6'}$ are hydrogen. In yet another embodiment, X is CR$^6$R$^{6'}$; R$^5$, R$^{5'}$, R$^6$ and R$^{6'}$ are hydrogen atoms and R$^7$ is dimethylamino.

In one embodiment, R$^9$ is hydrogen. In another embodiment, R$^9$ is substituted or unsubstituted aryl (e.g., phenyl or heteroaryl). In another embodiment, R$^9$ is substituted or unsubstituted alkyl. In a further embodiment, R$^9$ is aminoalkyl, e.g., aminomethyl (e.g., —CH$_2$—N$^{9n}$R$^{9m}$, wherein R$^{9n}$ is hydrogen or a prodrug and R$^{9m}$ is hydrogen or lower alkyl).

In another embodiment, R$^7$ is hydrogen. In yet another embodiment, R$^7$ is substituted or unsubstituted aryl, e.g., phenyl or heteroaryl (e.g., pyridinyl, pyrrolyl, pyrazinyl, etc.). In another embodiment, R$^7$ is substituted or unsubstituted amino (e.g., dimethylamino), nitro or halogen. In another embodiment, R$^8$ is hydrogen.

In another embodiment, R$^{4c}$ is hydrogen. In a further embodiment, R$^{4d}$ is also hydrogen. Alternatively, R$^{4d}$ is substituted or unsubstituted arylcarbonyl, arylaminocarbonyl, substituted or unsubstituted arylsulfonyl or alkylcarbonyl.

In another embodiment, the tetracycline compound is selected from the group consisting of:

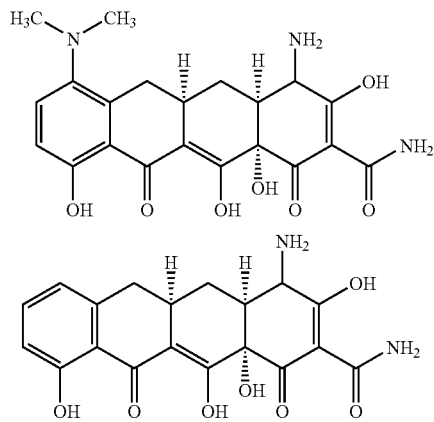

-continued

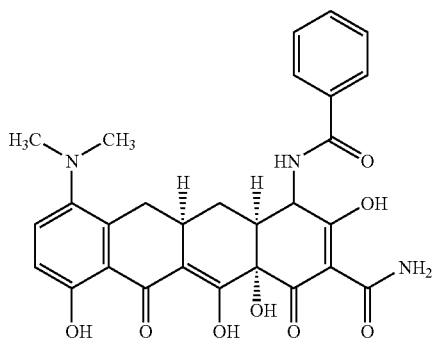
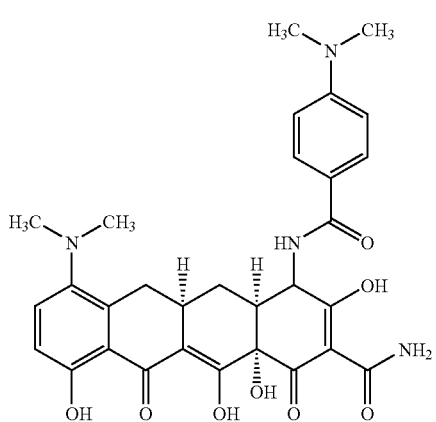
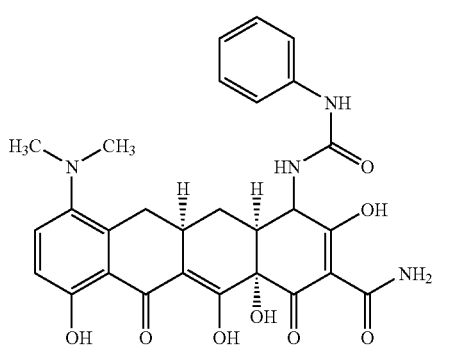
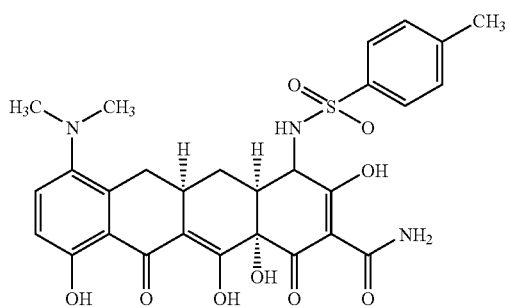

-continued

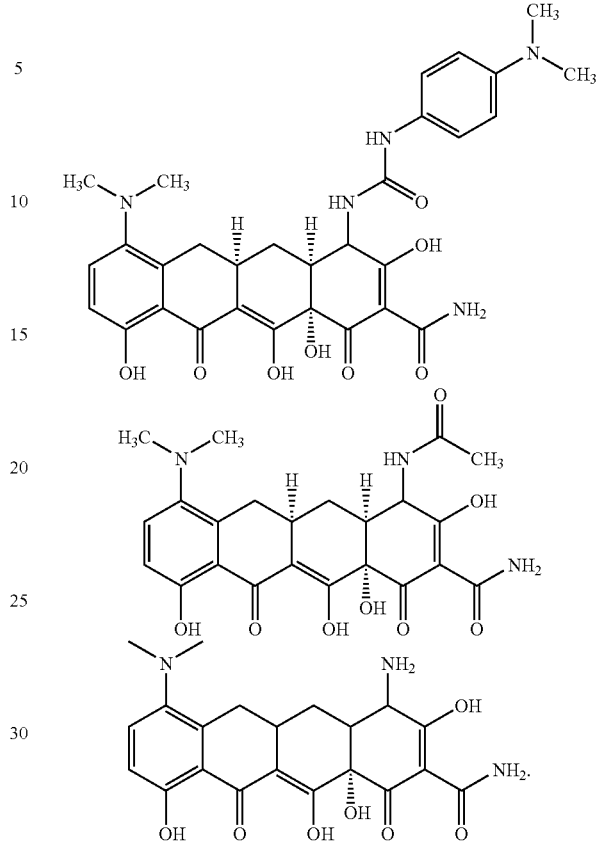

In one embodiment, the tetracycline compounds of the invention do not include those described in U.S. Ser. No. 09/660,598, 09/823,884, 09/852,908, 10/819,343, 10/820,456, 09/894,805, 09/895,796, 09/895,812, 09/895,797, 09/895,857, 10/097,634, 10/759,484, 10/337,914, 10/636,437, 10/752,378, or 10/740,961. The entire contents of each of these applications are hereby incorporated herein in their entirety.

In another embodiment, the tetracycline compounds of the invention do not include tetracycline compounds wherein $R^7$ is selected from the group consisting of hydrogen, amino, nitro, mono(lower alkyl)amino, halogen, di(lower alkyl) amino, ethoxythiocarbonylthio, azido, acylamino, diazonium, cyano, and hydroxyl; $R^{6'}$ is selected from the group consisting of hydrogen and methyl; $R^6$ and $R^5$ are selected from the group consisting of hydrogen and hydroxyl; $R^4$ is selected from the group consisting of NOH, N—NH—A, and NH—A, where A is a lower alkyl group; $R^8$ is selected from the group consisting of hydrogen and halogen; $R^9$ is selected from the group consisting of hydrogen, amino, azido, nitro, acylamino, hydroxy, ethoxythiocarbonylthio, mono(lower alkyl)amino, halogen, di(lower alkyl)amino and $RCH(NH_2)$ CO; R is hydrogen or lower alkyl; and pharmaceutically acceptable and unacceptable salts thereof. In another embodiment, the tetracycline compounds of the invention do not include the compounds described in U.S. Pat. No. 6,506,740, incorporated herein by reference in its entirety.

Methods for Synthesizing Tetracycline Compounds of the Invention

The tetracycline compounds of this invention can be synthesized using the methods described in the Schemes, Examples, and/or by other techniques known to those of ordinary skill in the art.

The substituted tetracycline compounds of the invention can be synthesized using the methods described in the following schemes and by using art recognized techniques. All novel substituted tetracycline compounds described herein are included in the invention as compounds.

SCHEME 1

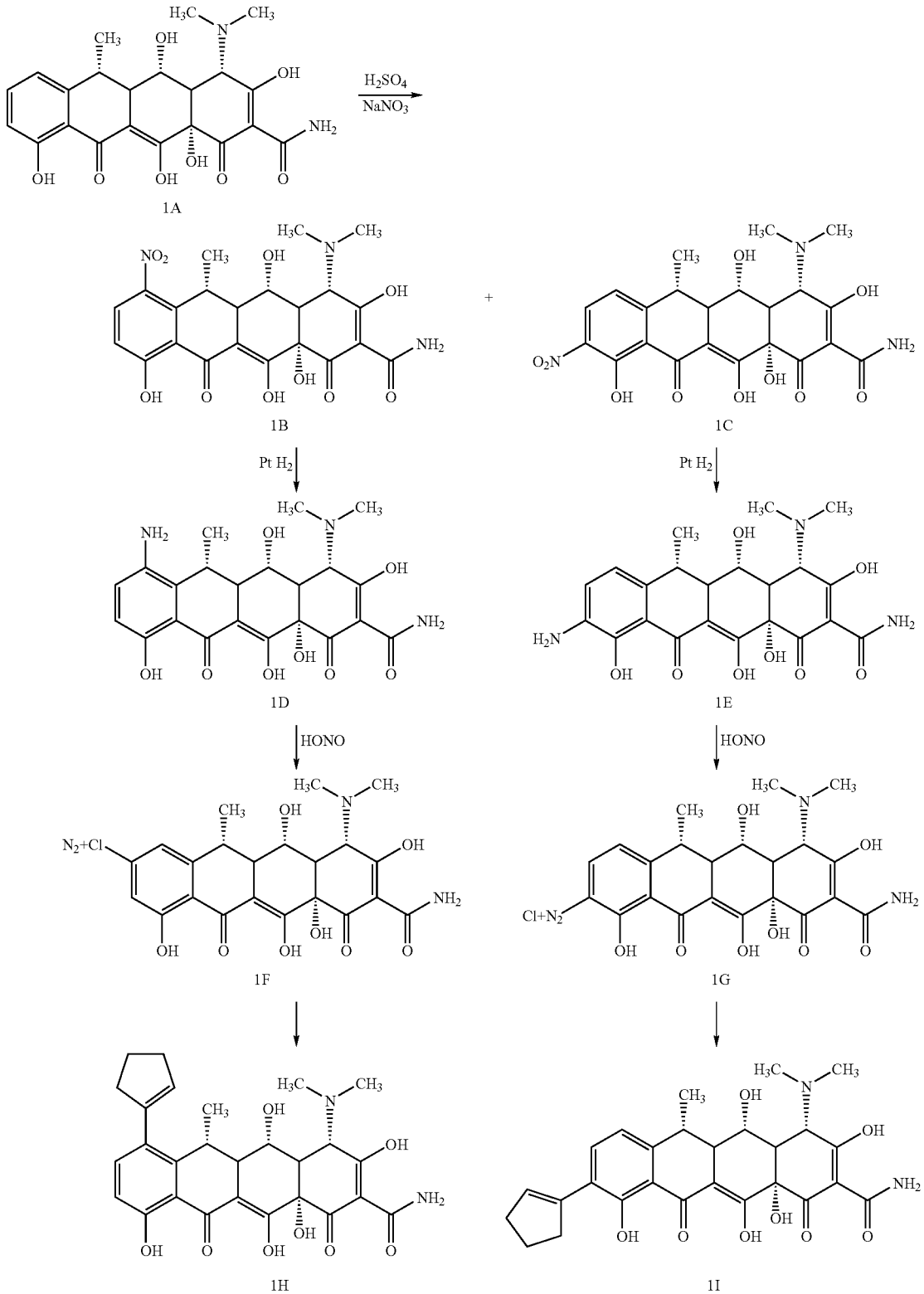

9- and 7-substituted tetracyclines can be synthesized by the method shown in Scheme 1. As shown in Scheme 1, 9- and 7-substituted tetracycline compounds can be synthesized by treating a tetracycline compound (e.g., doxycycline, 1A), with sulfuric acid and sodium nitrate. The resulting product is a mixture of the 7-nitro and 9-nitro isomers (1B and 1C, respectively). The 7-nitro (1B) and 9-nitro (1C) derivatives are treated by hydrogenation using hydrogen gas and a platinum catalyst to yield amines 1D and 1E. The isomers are separated at this time by conventional methods. To synthesize 7- or 9-substituted alkenyl derivatives, the 7- or 9-amino tetracycline compound (1E and 1F, respectively) is treated with HONO, to yield the diazonium salt (1G and 1H). The salt (1G and 1H) is treated with an appropriate reactive reagent to yield the desired compound(e.g., in Scheme 1, 7-cyclopent-1-enyl doxycycline (1H) and 9-cyclopent-1-enyl doxycycline (1I)).

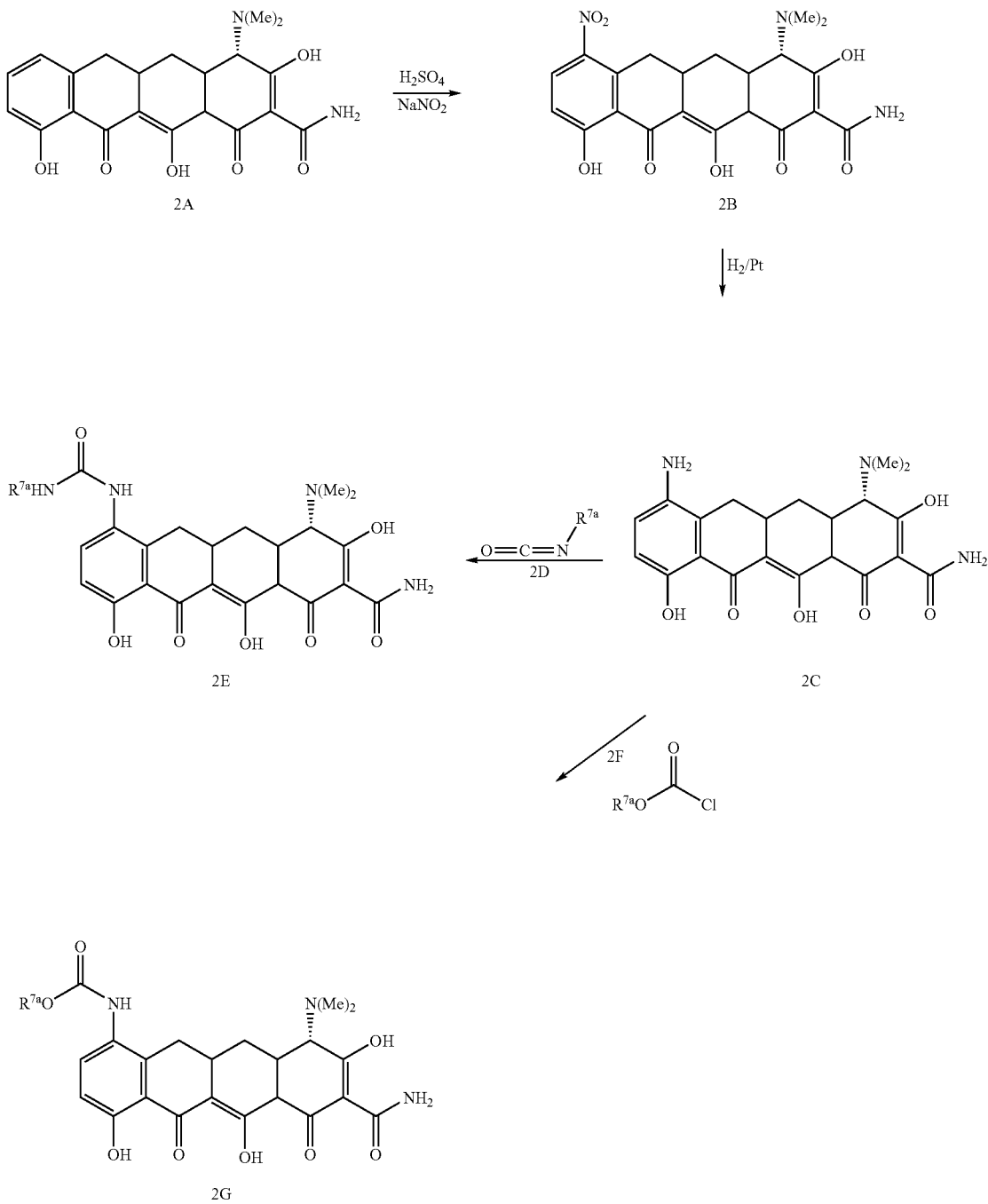

As shown in Scheme 2, tetracycline compounds of the invention wherein $R^7$ is a carbamate or a urea derivative can be synthesized using the following protocol. Sancycline (2A) is treated with $NaNO_2$ under acidic conditions forming 7-nitro sancycline (2B) in a mixture of positional isomers. 7-nitrosancycline (2B) is then treated with $H_2$ gas and a platinum catalyst to form the 7-amino sancycline derivative (2C). To form the urea derivative (2E), isocyanate (2D) is reacted with the 7-amino sancycline derivative (2C). To form the carbamate (2G), the appropriate acid chloride ester (2F) is reacted with 2C.

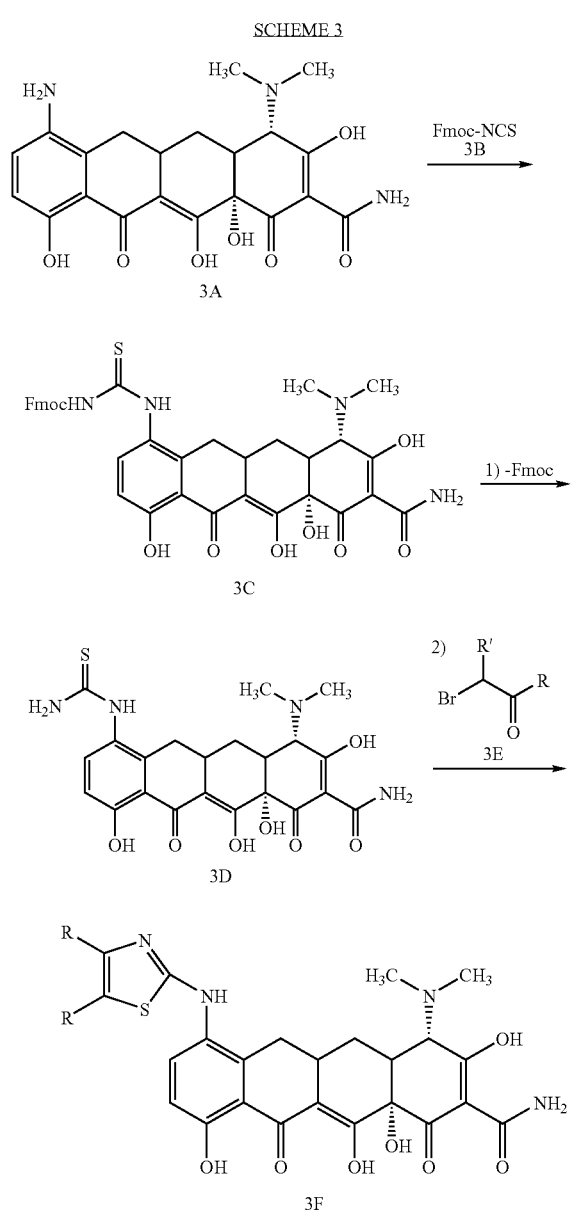

As shown in Scheme 3, tetracycline compounds of the invention, wherein $R^7$ is a heterocyclic (i.e. thiazole) substituted amino group can be synthesized using the above protocol. 7-amino sancycline (3A) is reacted with Fmoc-isothiocyanate (3B) to produce the protected thiourea (3C). The protected thiourea (3C) is then deprotected yielding the active sancycline thiourea (3D) compound. The sancycline thiourea (3D) is reacted with an α-haloketone (3E) to produce a thiazole substituted 7-amino sancycline (3F).

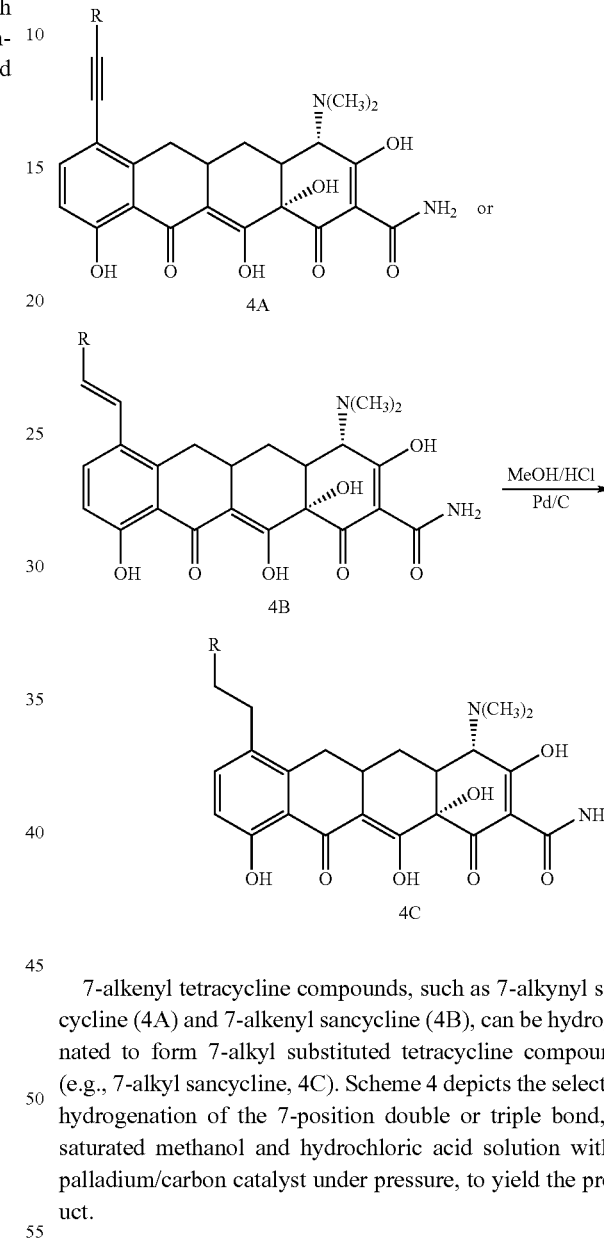

7-alkenyl tetracycline compounds, such as 7-alkynyl sancycline (4A) and 7-alkenyl sancycline (4B), can be hydrogenated to form 7-alkyl substituted tetracycline compounds (e.g., 7-alkyl sancycline, 4C). Scheme 4 depicts the selective hydrogenation of the 7-position double or triple bond, in saturated methanol and hydrochloric acid solution with a palladium/carbon catalyst under pressure, to yield the product.

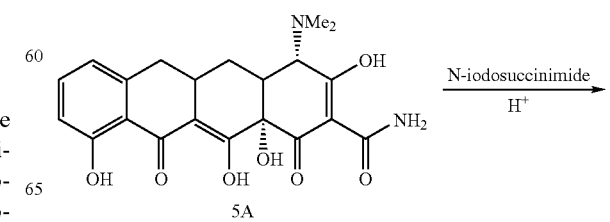

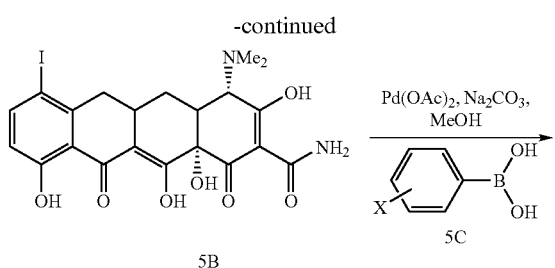

5B

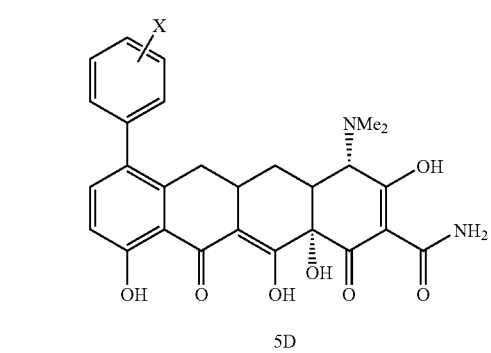

5D

In Scheme 5, a general synthetic scheme for synthesizing 7-position aryl derivatives is shown. A Suzuki coupling of an aryl boronic acid with an iodosancycline compound is shown. An iodo sancycline compound (5B) can be synthesized from sancycline by treating sancycline (5A) with at least one equivalent N-iodosuccinimide (NIS) under acidic conditions. The reaction is quenched, and the resulting 7-iodo sancycline (5B) can then be purified using standard techniques known in the art. To form the aryl derivative, 7-iodo sancycline (5B) is treated with an aqueous base (e.g., $Na_2CO_3$) and an appropriate boronic acid (5C) and under an inert atmosphere. The reaction is catalyzed with a palladium catalyst (e.g., $Pd(OAc)_2$). The product (5D) can be purified by methods known in the art (such as HPLC). Other 7-aryl, alkenyl, and alkynyl tetracycline compounds can be synthesized using similar protocols.

The 7-substituted tetracycline compounds of the invention can also be synthesized using Stille cross couplings. Stille cross couplings can be performed using an appropriate tin reagent (e.g., $R—SnBu_3$) and a halogenated tetracycline compound, (e.g., 7-iodosancycline). The tin reagent and the iodosancycline compound can be treated with a palladium catalyst (e.g., $Pd(PPh_3)_2Cl_2$ or $Pd(AsPh_3)_2Cl_2$) and, optionally, with an additional copper salt, e.g., CuI. The resulting compound can then be purified using techniques known in the art.

SCHEME 6

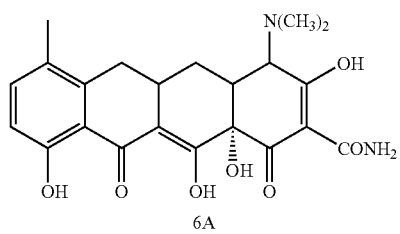

6A

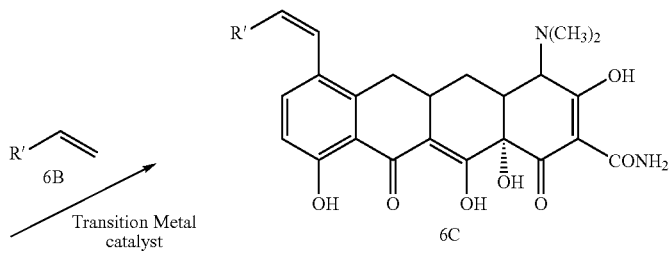

6C

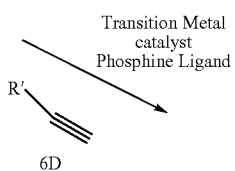

6D

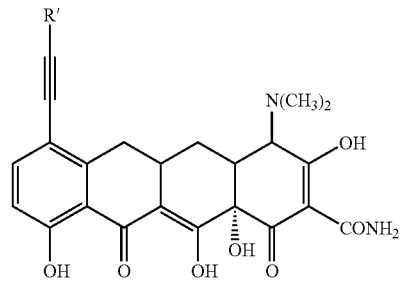

6E

The compounds of the invention can also be synthesized using Heck-type cross coupling reactions. As shown in Scheme 6, Heck-type cross-couplings can be performed by suspending a halogenated tetracycline compound (e.g., 7-iodosancycline, 6A) and an appropriate palladium or other transition metal catalyst (e.g., Pd(OAc)$_2$ and CuI) in an appropriate solvent (e.g., degassed acetonitrile). The substrate, a reactive alkene (6B) or alkyne (6D), and triethylamine are then added and the mixture is heated for several hours, before being cooled to room temperature. The resulting 7-substituted alkenyl (6C) or 7-substituted alkynyl (6E) tetracycline compound can then be purified using techniques known in the art.

To prepare 7-(2'-Chloro-alkenyl)-tetracycline compounds, the appropriate 7-(alkynyl)-sancycline (7A) is dissolved in saturated methanol and hydrochloric acid and stirred. The solvent is then removed to yield the product (7B).

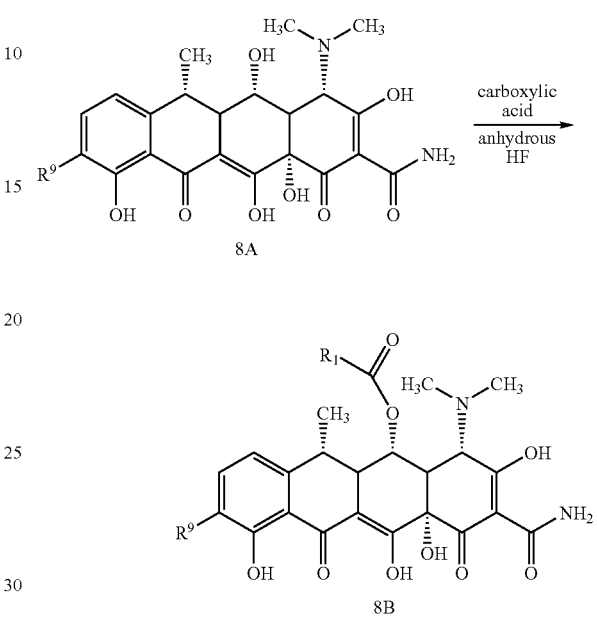

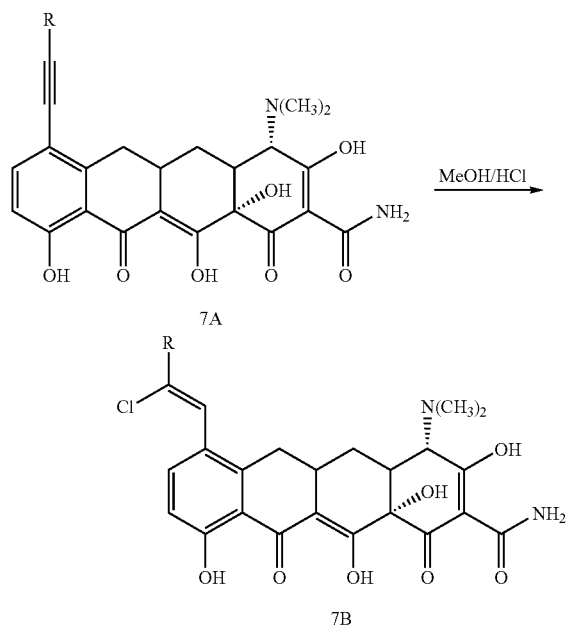

As depicted in Scheme 8, 5-esters of 9-substituted tetracycline compounds can be formed by dissolving the 9-substituted compounds (8A) in strong acid (e.g. HF, methanesulphonic acid, and trifluoromethanesulfonic acid) and adding the appropriate carboxylic acid to yield the corresponding esters (8B).

As shown in Scheme 9 below, 7 and 9 aminomethyl tetracyclines may be synthesized using reagents such as hydroxymethyl-carbamic acid benzyl ester.

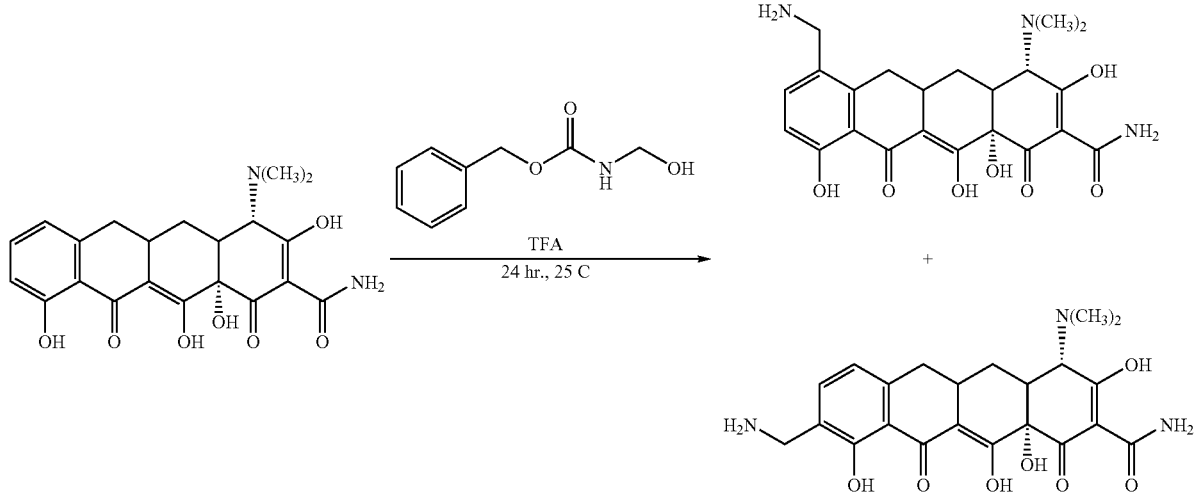

A method for derivatizing tetracycline compounds at the 4 position has been discovered through chemical modification via oxidation of the C4 position to produce a C4 oxime moiety. The oxime moiety is reduced to a C4 amino group as shown in Scheme 10:

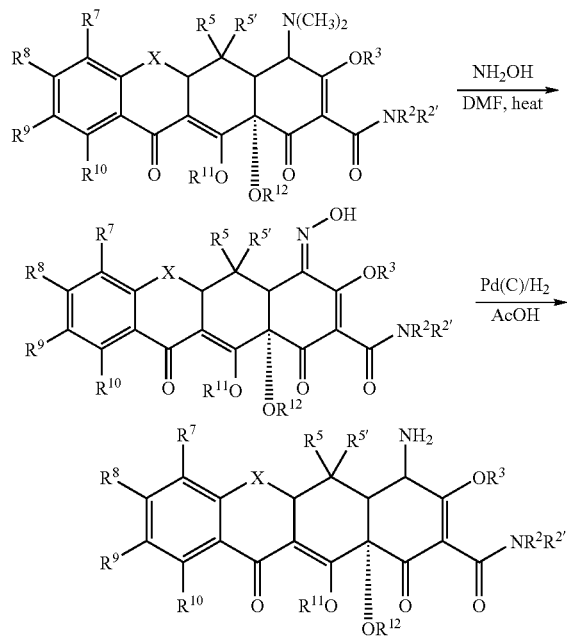

In one embodiment, the invention pertains to a method for synthesizing 4-substituted tetracycline compounds. The method includes contacting a tetracycline compound with an effective amount of an oxidizing agent to form a 4-oximesubstituted tetracycline compound, and contacting the 4-oxime-substituted tetracycline compound with a reducing agent, such that the 4-aminosubstituted tetracycline compound is formed.

The term "oxidizing agent" includes agents which are capable of oxidizing the C4 dialkylamine group to an oxime moiety. In one embodiment, the oxidizing agent is hydroxylamine.

Reducing agents are also known in the art. Examples of reducing agents are described in Comprehensive Organic Transformations ("COT") $2^{nd}$ Ed., Larock, 304, 305, incorporated herein by reference. In one embodiment, the reducing agent is palladium on carbon with hydrogen gas in the presence of acetic acid.

In one embodiment, the tetracycline compound is tetracycline, doxycycline, methacycline, minocycline, or sancycline. In another embodiment, the tetracycline compound is a tetracycline compound described in, for example, WO 03/079983, WO 02/12170, WO 02/04407, WO 02.04406, WO 02/04405, WO 02/04404, WO 01/74761, WO 03/079984, WO 03/075857, WO 03/057169, WO 02/072545, WO 02/072506, U.S. Ser. No. 10/619,653, U.S. Ser. No. 09/895,857; U.S. Ser. No. 09/895,812; U.S. Pat. No. 5,326, 759; U.S. Pat. No. 5,328,902; U.S. Pat. No. 5,495,031; U.S. Pat. No. 5,495,018; U.S. Pat. No. 5,495,030; U.S. Pat. No. 5,495,032; U.S. Pat. No. 5,512,553; U.S. Pat. No. 5,675,030; U.S. Pat. No. 5,843,925; U.S. Pat, No. 5,886,175; U.S. Pat. No. 6,165,999; U.S. Pat. No. 3,239,499; WO 95/22529; U.S. Pat. No. 5,064,821; U.S. Pat. No. 5,589,470; U.S. Pat. No. 5,811,412, or U.S. application Ser. No. 20040002481.

Tetracycline compounds of the invention can be synthesized using methods and reactive agents known in the art to react with amine groups. For example, acid chlorides are reactive agents which react to give tetracycline compounds of the inventions with various $R^4$ and $R^{4'}$ substituents (Scheme 11). Other reactive agents which can be used to synthesize the compounds of the invention with various $R^4$ and $R^{4'}$ substituents are sulfonyl halides, sulfonyl anhydrides, and isocyanates. Further reactive agents which can be used to synthesize the compounds of the invention with various $R^4$ and $R^{4'}$ substituents are aldehydes reacted under reducing conditions (Scheme 12).

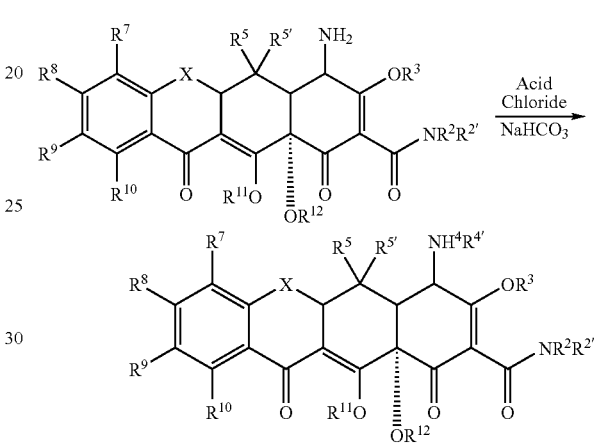

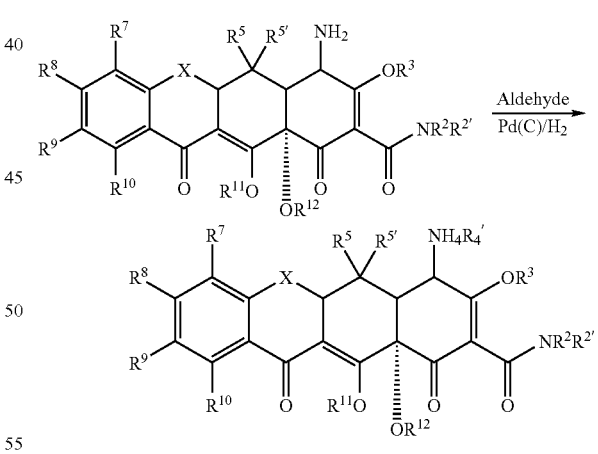

The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$-$C_6$ for straight chain, $C_3$-$C_6$ for branched chain), and more preferably 4 or fewer. Likewise, preferred cycloalkyls have from 3-8 carbon atoms in their ring structure, and more preferably have 5 or 6 carbons in the ring structure. The term $C_1$-$C_6$ includes alkyl groups containing 1 to 6 carbon atoms.

Moreover, the term alkyl includes both "unsubstituted alkyls" and "substituted alkyls", the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "arylalkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, arylalkyl aminocarbonyl, alkenylaminocarbonyl, alkylcarbonyl, arylcarbonyl, arylalkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethylenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2-5 carbon atoms.

The term "acyl" includes compounds and moieties which contain the acyl radical ($CH_3CO$—) or a carbonyl group. It includes substituted acyl moieties. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term includes "alkyl amino" which comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "carbonyl" or "carboxy" includes compounds and moieties which contain a carbon connected with a double bond to an oxygen atom. The carbonyl can be further substituted with any moiety which allows the compounds of the invention to perform its intended function. For example, carbonyl moieties may be substituted with alkyls, alkenyls, alkynyls, aryls, alkoxy, aminos, etc. Examples of moieties which contain a carbonyl include aldehydes, ketones, carboxylic acids, amides, esters, anhydrides, etc.

The term "thiocarbonyl" or "thiocarboxy" includes compounds and moieties which contain a carbon connected with a double bond to a sulfur atom.

The term "ether" includes compounds or moieties which contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "ester" includes compounds and moieties which contain a carbon or a heteroatom bound to an oxygen atom which is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom which is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O—.

The term "halogen" includes fluorine, bromine, chlorine, iodine, etc. The term "perhalogenated" generally refers to a moiety wherein all hydrogens are replaced by halogen atoms.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, arylalkylaminocarbonyl, alkenylaminocarbonyl, alkylcarbonyl, arylcarbonyl, arylalkyl carbonyl, alkenylcarbonyl, aminocarbonyl, alkylthiocarbonyl, alkoxyl, phosphate, phosphonato, phosphinato, cyano, amido, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

The term "prodrug moiety" includes moieties which can be metabolized in vivo to a hydroxyl group and moieties which may advantageously remain esterified in vivo. Preferably, the prodrugs moieties are metabolized in vivo by esterases or by other mechanisms to hydroxyl groups or other advantageous groups. Examples of prodrugs and their uses are well known in the art (See, e.g., Berge et al. (1977) "Pharmaceutical Salts", *J. Pharm. Sci.* 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters.

It will be noted that the structure of some of the tetracycline compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

Methods for Treating Tetracycline Responsive States

The invention also pertains to methods for treating a tetracycline responsive states in subjects, by administering to a subject an effective amount of a tetracycline compound of the invention (e.g., a compound of Formula I or II, or otherwise described herein), such that the tetracycline responsive state is treated.

The term "treating" includes curing as well as ameliorating at least one symptom of the state, disease or disorder, e.g., the tetracycline compound responsive state.

The language "tetracycline compound responsive state" or "tetracycline responsive state" includes states which can be treated, prevented, or otherwise ameliorated by the administration of a tetracycline compound of the invention. Tetracycline compound responsive states include bacterial, viral, and fungal infections (including those which are resistant to other tetracycline compounds), cancer (e.g., prostate, breast, colon, lung melanoma and lymph cancers and other disorders characterized by unwanted cellular proliferation, including, but not limited to, those described in U.S. Pat. No. 6,100,248), arthritis, osteoporosis, diabetes, and other states for which tetracycline compounds have been found to be active (see, for example, U.S. Pat. Nos. 5,789,395; 5,834,450; 6,277,061 and 5,532,227, each of which is expressly incorporated herein by reference). Compounds of the invention can be used to prevent or control important mammalian and veterinary diseases such as diarrhea, urinary tract infections, infections of skin and skin structure, ear, nose and throat infections, wound infection, mastitis and the like. In addition, methods for treating neoplasms using tetracycline compounds of the invention are also included (van der Bozert et al., *Cancer Res.,* 48:6686-6690 (1988)). In a further embodiment, the tetracycline responsive state is not a bacterial infection. In another embodiment, the tetracycline compounds of the invention are essentially non-antibacterial. For example, non-antibacterial tetracycline compounds of the invention may have MIC values greater than about 4 μg/ml (as measured by assays known in the art and/or the assay given in Example 9).

Tetracycline compound responsive states also include inflammatory process associated states (IPAS). The term "inflammatory process associated state" includes states in which inflammation or inflammatory factors (e.g., matrix metalloproteinases (MMPs), nitric oxide (NO), TNF, interleukins, plasma proteins, cellular defense systems, cytokines, lipid metabolites, proteases, toxic radicals, adhesion molecules, etc.) are involved or are present in an area in aberrant amounts, e.g., in amounts which may be advantageous to alter, e.g., to benefit the subject. The inflammatory process is the response of living tissue to damage. The cause of inflammation may be due to physical damage, chemical substances, micro-organisms, tissue necrosis, cancer or other agents. Acute inflammation is short-lasting, lasting only a few days. If it is longer lasting however, then it may be referred to as chronic inflammation.

IPAF's include inflammatory disorders. Inflammatory disorders are generally characterized by heat, redness, swelling, pain and loss of function. Examples of causes of inflammatory disorders include, but are not limited to, microbial infections (e.g., bacterial and fungal infections), physical agents (e.g., burns, radiation, and trauma), chemical agents (e.g., toxins and caustic substances), tissue necrosis and various types of immunologic reactions.

Examples of inflammatory disorders include, but are not limited to, osteoarthritis, rheumatoid arthritis, acute and chronic infections (bacterial and fungal, including diphtheria and pertussis); acute and chronic bronchitis, sinusitis, and upper respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendinitis); uremic pericarditis; acute and chronic cholecystis; acute and chronic vaginitis; acute and chronic uveitis; drug reactions; insect bites; burns (thermal, chemical, and electrical); and sunburn.

Tetracycline compound responsive states also include NO associated states. The term "NO associated state" includes states which involve or are associated with nitric oxide (NO) or inducible nitric oxide synthase (iNOS). NO associated state includes states which are characterized by aberrant amounts of NO and/or iNOS. Preferably, the NO associated state can be treated by administering tetracycline compounds of the invention. The disorders, diseases and states described in U.S. Pat. Nos. 6,231,894; 6,015,804; 5,919,774; and 5,789, 395 are also included as NO associated states. The entire contents of each of these patents are hereby incorporated herein by reference.

Other examples of NO associated states include, but are not limited to, malaria, senescence, diabetes, vascular stroke, neurodegenerative disorders (Alzheimer's disease & Huntington's disease), cardiac disease (reperfusion-associated injury following infarction), juvenile diabetes, inflammatory disorders, osteoarthritis, rheumatoid arthritis, acute, recurrent and chronic infections (bacterial, viral and fungal); acute and chronic bronchitis, sinusitis, and respiratory infections, including the common cold; acute and chronic gastroenteritis and colitis; acute and chronic cystitis and urethritis; acute and chronic dermatitis; acute and chronic conjunctivitis; acute and chronic serositis (pericarditis, peritonitis, synovitis, pleuritis and tendonitis); uremic pericarditis; acute and chronic cholecystis; cystic fibrosis, acute and chronic vaginitis; acute and chronic uveitis; drug reactions; insect bites; burns (thermal, chemical, and electrical); and sunburn.

The term "inflammatory process associated state" also includes, in one embodiment, matrix metalloproteinase associated states (MMPAS). MMPAS include states characterized by aberrant amounts of MMPs or MMP activity. These are also include as tetracycline compound responsive states which may be treated using compounds of the invention.

Examples of matrix metalloproteinase associated states ("MMPAS's") include, but are not limited to, arteriosclerosis, corneal ulceration, emphysema, osteoarthritis, multiple sclerosis(Liedtke et al., *Ann. Neurol.* 1998, 44:35-46; Chandler et al., *J. Neuroimmunol.* 1997, 72:155-71), osteosarcoma, osteomyelitis, bronchiectasis, chronic pulmonary obstructive disease, skin and eye diseases, periodontitis, osteoporosis, rheumatoid arthritis, ulcerative colitis, inflammatory disorders, tumor growth and invasion (Stetler-Stevenson et al., *Annu. Rev. Cell Biol.* 1993, 9:541-73; Tryggvason et al., *Biochim. Biophys. Acta* 1987, 907:191-217; Li et al., *Mol. Carcinog.* 1998, 22:84-89)),metastasis, acute lung injury, stroke, ischemia, diabetes, aortic or vascular aneurysms, skin tissue wounds, dry eye, bone and cartilage degradation (Greenwald et al., *Bone* 1998, 22:33-38; Ryan et al., *Curr. Op. Rheumatol.* 1996, 8;238-247). Other MMPAS include those described in U.S. Pat. Nos. 5,459,135; 5,321,017; 5,308,839; 5,258,371; 4,935,412; 4,704,383, 4,666,897, and RE 34,656, incorporated herein by reference in their entirety.

In another embodiment, the tetracycline compound responsive state is cancer. Examples of cancers which the tetracycline compounds of the invention may be useful to treat include all solid tumors, i.e., carcinomas e.g., adenocarcinomas, and sarcomas. Adenocarcinomas are carcinomas derived from glandular tissue or in which the tumor cells form recognizable glandular structures. Sarcomas broadly include tumors whose cells are embedded in a fibrillar or homogeneous substance like embryonic connective tissue. Examples of carcinomas which may be treated using the methods of the invention include, but are not limited to, carcinomas of the prostate, breast, ovary, testis, lung, colon, and breast. The methods of the invention are not limited to the treatment of these tumor types, but extend to any solid tumor derived from any organ system. Examples of treatable cancers include, but are not limited to, colon cancer, bladder cancer, breast cancer, melanoma, ovarian carcinoma, prostatic carcinoma, lung cancer, and a variety of other cancers as well. The methods of the invention also cause the inhibition of cancer growth in adenocarcinomas, such as, for example, those of the prostate, breast, kidney, ovary, testes, and colon.

In an embodiment, the tetracycline responsive state of the invention is cancer. The invention pertains to a method for treating a subject suffering or at risk of suffering from cancer, by administering an effective amount of a substituted tetracycline compound, such that inhibition cancer cell growth occurs, i.e., cellular proliferation, invasiveness, metastasis, or tumor incidence is decreased, slowed, or stopped. The inhibition may result from inhibition of an inflammatory process, down-regulation of an inflammatory process, some other mechanism, or a combination of mechanisms. Alternatively, the tetracycline compounds may be useful for preventing cancer recurrence, for example, to treat residual cancer following surgical resection or radiation therapy. The tetracycline compounds useful according to the invention are especially advantageous as they are substantially non-toxic compared to other cancer treatments. In a further embodiment, the compounds of the invention are administered in combination with standard cancer therapy, such as, but not limited to, chemotherapy.

Examples of tetracycline responsive states also include neurological disorders which include both neuropsychiatric and neurodegenerative disorders, but are not limited to, such as Alzheimer's disease, dementias related to Alzheimer's disease (such as Pick's disease), Parkinson's and other Lewy diffuse body diseases, senile dementia, Huntington's disease, Gilles de la Tourette's syndrome, multiple sclerosis, amylotrophic lateral sclerosis (ALS), progressive supranuclear palsy, epilepsy, and Creutzfeldt-Jakob disease; autonomic function disorders such as hypertension and sleep disorders, and neuropsychiatric disorders, such as depression, schizophrenia, schizoaffective disorder, Korsakoff's psychosis, mania, anxiety disorders, or phobic disorders; learning or memory disorders, e.g., amnesia or age-related memory loss, attention deficit disorder, dysthymic disorder, major depressive disorder, mania, obsessive-compulsive disorder, psychoactive substance use disorders, anxiety, phobias, panic disorder, as well as bipolar affective disorder, e.g., severe bipolar affective (mood) disorder (BP-1), bipolar affective neurological disorders, e.g., migraine and obesity. Further neurological disorders include, for example, those listed in the American Psychiatric Association's Diagnostic and Statistical manual of Mental Disorders (DSM), the most current version of which is incorporated herein by reference in its entirety.

Other examples of tetracycline compound responsive states are described in WO 03/005971A2 and U.S. Patent Application Publication No. 20040214800, each incorporated herein by reference.

The language "in combination with" another therapeutic agent or treatment includes co-administration of the tetracycline compound, (e.g., inhibitor) and with the other therapeutic agent or treatment, administration of the tetracycline compound first, followed by the other therapeutic agent or treatment and administration of the other therapeutic agent or treatment first, followed by the tetracycline compound. The other therapeutic agent may be any agent which is known in the art to treat, prevent, or reduce the symptoms of an IPAS. Furthermore, the other therapeutic agent may be any agent of benefit to the patient when administered in combination with the administration of an tetracycline compound. In one embodiment, the cancers treated by methods of the invention include those described in U.S. Pat. Nos. 6,100,248; 5,843, 925; 5,837,696; or 5,668,122, incorporated herein by reference in their entirety.

In another embodiment, the tetracycline compound responsive state is diabetes, e.g., juvenile diabetes, diabetes mellitus, diabetes type I, or diabetes type II. In a further embodiment, protein glycosylation is not affected by the administration of the tetracycline compounds of the invention. In another embodiment, the tetracycline compound of the invention is administered in combination with standard diabetic therapies, such as, but not limited to insulin therapy. In a further embodiment, the IPAS includes disorders described in U.S. Pat. Nos. 5,929,055; and 5,532,227, incorporated herein by reference in their entirety.

In another embodiment, the tetracycline compound responsive state is a bone mass disorder. Bone mass disorders include disorders where a subjects bones are disorders and states where the formation, repair or remodeling of bone is advantageous. For examples bone mass disorders include osteoporosis (e.g., a decrease in bone strength and density), bone fractures, bone formation associated with surgical procedures (e.g., facial reconstruction), osteogenesis imperfecta (brittle bone disease), hypophosphatasia, Paget's disease, fibrous dysplasia, osteopetrosis, myeloma bone disease, and the depletion of calcium in bone, such as that which is related to primary hyperparathyroidism. Bone mass disorders include all states in which the formation, repair or remodeling of bone is advantageous to the subject as well as all other disorders associated with the bones or skeletal system of a subject which can be treated with the tetracycline compounds of the invention. In a further embodiment, the bone mass disorders include those described in U.S. Pat. Nos. 5,459,135; 5,231,017; 5,998,390; 5,770,588; RE 34,656; U.S. Pat. Nos. 5,308,839; 4,925,833; 3,304,227; and 4,666,897, each of which is hereby incorporated herein by reference in its entirety.

In another embodiment, the tetracycline compound responsive state is acute lung injury. Acute lung injuries include adult respiratory distress syndrome (ARDS), post-pump syndrome (PPS), and trauma. Trauma includes any injury to living tissue caused by an extrinsic agent or event. Examples of trauma include, but are not limited to, crush injuries, contact with a hard surface, or cutting or other damage to the lungs.

The invention also pertains to a method for treating acute lung injury by administering a substituted tetracycline compound of the invention.

The tetracycline responsive states of the invention also include chronic lung disorders. The invention pertains to methods for treating chronic lung disorders by administering a tetracycline compound, such as those described herein. The method includes administering to a subject an effective amount of a substituted tetracycline compound such that the chronic lung disorder is treated. Examples of chronic lung disorders include, but are not limited, to asthma, cystic fibrosis, and emphesema. In a further embodiment, the tetracycline compounds of the invention used to treat acute and/or chronic lung disorders such as those described in U.S. Pat. Nos. 5,977,091; 6,043,231; 5,523,297; and 5,773,430, each of which is hereby incorporated herein by reference in its entirety.

In yet another embodiment, the tetracycline compound responsive state is ischemia, stroke, or ischemic stroke. The invention also pertains to a method for treating ischemia, stroke, or ischemic stroke by administering an effective amount of a substituted tetracycline compound of the invention. In a further embodiment, the tetracycline compounds of the invention are used to treat such disorders as described in U.S. Pat. Nos. 6,231,894; 5,773,430; 5,919,775 or 5,789,395, incorporated herein by reference.

In another embodiment, the tetracycline compound responsive state is a skin wound. The invention also pertains, at least in part, to a method for improving the healing response of the epithelialized tissue (e.g., skin, mucusae) to acute traumatic injury (e.g., cut, burn, scrape, etc.). The method may include using a tetracycline compound of the invention (which may or may not have antibacterial activity) to improve the capacity of the epithelialized tissue to heal acute wounds. The method may increase the rate of collagen accumulation of the healing tissue. The method may also decrease the proteolytic activity in the epthithelialized tissue by decreasing the collagenolytic and/or gellatinolytic activity of MMPs. In a further embodiment, the tetracycline compound of the invention is administered to the surface of the skin (e.g., topically). In a further embodiment, the tetracycline compound of the invention used to treat a skin wound, and other such disorders as described in, for example, U.S. Pat. Nos. 5,827,840; 4,704,383; 4,935,412; 5,258,371; 5,308,839, 5,459,135; 5,532,227; and 6,015,804; each of which is incorporated herein by reference in its entirety.

In yet another embodiment, the tetracycline compound responsive state is an aortic or vascular aneurysm in vascular tissue of a subject (e.g., a subject having or at risk of having an aortic or vascular aneurysm, etc.). The tetracycline compound may by effective to reduce the size of the vascular aneurysm or it may be administered to the subject prior to the onset of the vascular aneurysm such that the aneurysm is prevented. In one embodiment, the vascular tissue is an artery, e.g., the aorta, e.g., the abdominal aorta. In a further embodiment, the tetracycline compounds of the invention are used to treat disorders described in U.S. Pat. Nos. 6,043,225 and 5,834,449, incorporated herein by reference in their entirety.

Bacterial infections may be caused by a wide variety of gram positive and gram negative bacteria. The compounds of the invention are useful as antibiotics against organisms which are resistant to other tetracycline compounds. The antibiotic activity of the tetracycline compounds of the invention may be determined using the method discussed in Example 9, or by using the in vitro standard broth dilution method described in Waitz, J. A., *National Commission for Clinical Laboratory Standards, Document M7-A2*, vol. 10, no. 8, pp. 13-20, $2^{nd}$ edition, Villanova, Pa. (1990).

The tetracycline compounds may also be used to treat infections traditionally treated with tetracycline compounds such as, for example, rickettsiae; a number of gram-positive and gram-negative bacteria; and the agents responsible for lymphogranuloma venereum, inclusion conjunctivitis, psittacosis. The tetracycline compounds may be used to treat infections of, e.g., *K. pneumoniae, Salmonella, E. hirae, A. baumanii, B. catarrhalis, H. influenzae, P. aeruginosa, E. faecium, E. coli, S. aureus* or *E. faecalis*. In one embodiment, the tetracycline compound is used to treat a bacterial infection that is resistant to other tetracycline antibiotic compounds. The tetracycline compound of the invention may be administered with a pharmaceutically acceptable carrier.

The language "effective amount" of the compound is that amount necessary or sufficient to treat or prevent a tetracycline compound responsive state. The effective amount can vary, depending on such factors as the size and weight of the subject, the type of illness, or the particular tetracycline compound. For example, the choice of the tetracycline compound can affect what constitutes an "effective amount". One of ordinary skill in the art would be able to study the aforementioned factors and make the determination regarding the effective amount of the tetracycline compound without undue experimentation.

The invention also pertains to methods of treatment against microorganism infections and associated diseases. The methods include administration of an effective amount of one or more tetracycline compounds to a subject. The subject can be either a plant or, advantageously, an animal, e.g., a mammal, e.g., a human.

In the therapeutic methods of the invention, one or more tetracycline compounds of the invention may be administered alone to a subject, or more typically a compound of the invention will be administered as part of a pharmaceutical composition in mixture with conventional excipient, i.e., pharmaceutically acceptable organic or inorganic carrier substances suitable for parenteral, oral or other desired administration and which do not deleteriously react with the active compounds and are not deleterious to the recipient thereof.

Pharmaceutical Compositions of the Invention

The invention also pertains to pharmaceutical compositions comprising a therapeutically effective amount of a tetracycline compound (e.g., a compound of Formula I or II or any other compound described herein) and, optionally, a pharmaceutically acceptable carrier.

The language "pharmaceutically acceptable carrier" includes substances capable of being coadministered with the tetracycline compound(s), and which allow both to perform their intended function, e.g., treat or prevent a tetracycline responsive state. Suitable pharmaceutically acceptable carriers include but are not limited to water, salt solutions, alcohol, vegetable oils, polyethylene glycols, gelatin, lactose, amylose, magnesium stearate, talc, silicic acid, viscous paraffin, perfume oil, fatty acid monoglycerides and diglycerides, petroethral fatty acid esters, hydroxymethyl-cellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously react with the active compounds of the invention.

The tetracycline compounds of the invention that are basic in nature are capable of forming a wide variety of salts with various inorganic and organic acids. The acids that may be used to prepare pharmaceutically acceptable acid addition salts of the tetracycline compounds of the invention that are basic in nature are those that form non-toxic acid addition salts, i.e., salts containing pharmaceutically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and palmoate [i.e., 1,1'-methylene-bis-(2-hydroxy-3-naphthoate)] salts. Although such salts must be pharmaceutically acceptable for administration to a subject, e.g., a mammal, it is often desirable in practice to initially isolate a tetracycline compound of the invention from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The preparation of other tetracycline compounds of the invention not specifically described in the foregoing experimental section can be accomplished using combinations of the reactions described above that will be apparent to those skilled in the art.

The preparation of other tetracycline compounds of the invention not specifically described in the foregoing experimental section can be accomplished using combinations of the reactions described above that will be apparent to those skilled in the art.

The tetracycline compounds of the invention that are acidic in nature are capable of forming a wide variety of base salts. The chemical bases that may be used as reagents to prepare pharmaceutically acceptable base salts of those tetracycline compounds of the invention that are acidic in nature are those that form non-toxic base salts with such compounds. Such non-toxic base salts include, but are not limited to those derived from such pharmaceutically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines. The pharmaceutically acceptable base addition salts of tetracycline compounds of the invention that are acidic in nature may be formed with pharmaceutically acceptable cations by conventional methods. Thus, these salts may be readily prepared by treating the tetracycline compound of the invention with an aqueous solution of the desired pharmaceutically acceptable cation and evaporating the resulting solution to dryness, preferably under reduced pressure. Alternatively, a lower alkyl alcohol solution of the tetracycline compound of the invention may be mixed with an alkoxide of the desired metal and the solution subsequently evaporated to dryness.

The preparation of other tetracycline compounds of the invention not specifically described in the foregoing experimental section can be accomplished using combinations of the reactions described above that will be apparent to those skilled in the art.

The tetracycline compounds of the invention and pharmaceutically acceptable salts thereof can be administered via either the oral, parenteral or topical routes. In general, these compounds are most desirably administered in effective dosages, depending upon the weight and condition of the subject being treated and the particular route of administration chosen. Variations may occur depending upon the species of the subject being treated and its individual response to said medicament, as well as on the type of pharmaceutical formulation chosen and the time period and interval at which such administration is carried out.

The pharmaceutical compositions of the invention may be administered alone or in combination with other known compositions for treating tetracycline responsive states in a subject, e.g., a mammal. Preferred mammals include pets (e.g., cats, dogs, ferrets, etc.), farm animals (cows, sheep, pigs, horses, goats, etc.), lab animals (rats, mice, monkeys, etc.), and primates (chimpanzees, humans, gorillas). The language "in combination with" a known composition is intended to include simultaneous administration of the composition of the invention and the known composition, administration of the composition of the invention first, followed by the known composition and administration of the known composition first, followed by the composition of the invention. Any of the therapeutically composition known in the art for treating tetracycline responsive states can be used in the methods of the invention.

The tetracycline compounds of the invention may be administered alone or in combination with pharmaceutically acceptable carriers or diluents by any of the routes previously mentioned, and the administration may be carried out in single or multiple doses. For example, the novel therapeutic agents of this invention can be administered advantageously in a wide variety of different dosage forms, i.e., they may be combined with various pharmaceutically acceptable inert carriers in the form of tablets, capsules, lozenges, troches, hard candies, powders, sprays (e.g., aerosols, etc.), creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof. The compositions of the invention may be formulated such that the tetracycline compositions are released over a period of time after administration.

For parenteral administration (including intraperitoneal, subcutaneous, intravenous, intradermal or intramuscular injection), solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art. For parenteral application, examples of suitable preparations include solutions, preferably oily or aqueous solutions as well as suspensions, emulsions, or implants, including suppositories. Therapeutic compounds may be formulated in sterile form in multiple or single dose formats such as being dispersed in a fluid carrier such as sterile physiological saline or 5% saline dextrose solutions commonly used with injectables.

Additionally, it is also possible to administer the compounds of the present invention topically when treating inflammatory conditions of the skin. Examples of methods of topical administration include transdermal, buccal or sublingual application. For topical applications, therapeutic compounds can be suitably admixed in a pharmacologically inert topical carrier such as a gel, an ointment, a lotion or a cream. Such topical carriers include water, glycerol, alcohol, propylene glycol, fatty alcohols, triglycerides, fatty acid esters, or mineral oils. Other possible topical carriers are liquid petrolatum, isopropylpalmitate, polyethylene glycol, ethanol 95%, polyoxyethylene monolauriate 5% in water, sodium lauryl sulfate 5% in water, and the like. In addition, materials such as anti-oxidants, humectants, viscosity stabilizers and the like also may be added if desired.

For enteral application, particularly suitable are tablets, dragees or capsules having talc and/or carbohydrate carrier binder or the like, the carrier preferably being lactose and/or corn starch and/or potato starch. A syrup, elixir or the like can be used wherein a sweetened vehicle is employed. Sustained release compositions can be formulated including those wherein the active component is protected with differentially degradable coatings, e.g., by microencapsulation, multiple coatings, etc.

In addition to treatment of human subjects, the therapeutic methods of the invention also will have significant veterinary applications, e.g. for treatment of livestock such as cattle, sheep, goats, cows, swine and the like; poultry such as chickens, ducks, geese, turkeys and the like; horses; and pets such as dogs and cats. Also, the compounds of the invention may be used to treat non-animal subjects, such as plants.

It will be appreciated that the actual preferred amounts of active compounds used in a given therapy will vary according to the specific compound being utilized, the particular compositions formulated, the mode of application, the particular site of administration, etc. Optimal administration rates for a given protocol of administration can be readily ascertained by those skilled in the art using conventional dosage determination tests conducted with regard to the foregoing guidelines.

In general, compounds of the invention for treatment can be administered to a subject in dosages used in prior tetracycline therapies. See, for example, the *Physicians' Desk Reference*. For example, a suitable effective dose of one or more compounds of the invention will be in the range of from 0.01 to 100 milligrams per kilogram of body weight of recipient per day, preferably in the range of from 0.1 to 50 milligrams per kilogram body weight of recipient per day, more preferably in the range of 1 to 20 milligrams per kilogram body weight of recipient per day. The desired dose is suitably administered once daily, or several sub-doses, e.g. 2 to 5 sub-doses, are administered at appropriate intervals through the day, or other appropriate schedule. It will also be understood that normal, conventionally known precautions will be taken regarding the administration of tetracyclines generally to ensure their efficacy under normal use circumstances. Especially when employed for therapeutic treatment of humans and animals in vivo, the practitioner should take all sensible precautions to avoid conventionally known contradictions and toxic effects. Thus, the conventionally recognized adverse reactions of gastrointestinal distress and inflammations, the renal toxicity, hypersensitivity reactions, changes in blood, and impairment of absorption through aluminum, calcium, and magnesium ions should be duly considered in the conventional manner.

Furthermore, the invention also pertains to the use of a tetracycline compound of formula I, II, or any other compound described herein, for the preparation of a medicament. The medicament may include a pharmaceutically acceptable carrier and the tetracycline compound is an effective amount, e.g., an effective amount to treat a tetracycline responsive state.

EXEMPLIFICATION OF THE INVENTION

Compounds of the invention may be made as described below and/or by using literature techniques known to those of ordinary skill of the art.

Example 1

Synthesis of 4-Oximinominocycline

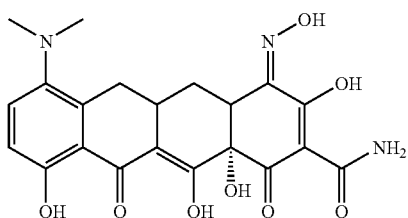

To a solution of minocycline 2HCL (29.3 g, 60.6 mmol) in DMF (300 mL) was a 1:1 solution of hydroxylamine:water (7.98 mL, 120 mmol). The solution was heated to 80° C. for 2 hours while exposed to air. After cooling to room temperature, the solution was diluted with water (2 L). The water solution was filtered through a plug of DVB resin eluting with a 500 mL gradient of acetonitrile and water (5%-10%-20%-50%). At the 50% gradient, the product elutes as a yellow solution. The solution was concentrated under reduced pressure and further dried under vacuum to afford 12 g as a yellow/orange solid in 45% yield.

Example 2

Synthesis of 4-Oximinosancycline

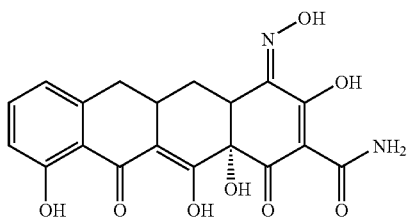

To a solution of sancycline hydrate (8.29 g, 20.0 mmol) in DMF (100 mL) was added a 1:1 solution of hydroxylamine: water (2.70 mL, 40.0 mmol). The solution was heated to 80° C. for 2 hours while exposed to air. After cooling to room temperature, the solution was diluted with water (2 L). The water solution was filtered through a plug of DVB resin eluting with a 500 mL gradient of acetonitrile and water (5%-10%-20%-50%). At the 50% gradient, the product elutes as a yellow solution. The solution was concentrated under reduced pressure and further dried under vacuum to afford 3.7 g as a yellow/orange solid in 46% yield.

Example 3

Synthesis of 4-Aminominocycline

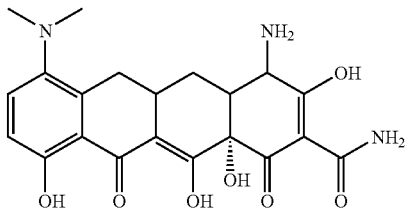

To a solution of 4-oximinominocycline (11.1 g, 25.0 mmol) in methanol (250 mL) and acetic acid (7.22 mL, 125 mmol) was added 5% palladium on carbon. The solution was flushed with hydrogen and placed under vacuum for three successive cycles. After the final cycle, the flask was placed under 50 psi of hydrogen for 16 hours. After flushing the flask with nitrogen and placing it under vacuum for three successive cycles, the solution was filtered through a plug of celite, while rinsing with methanol. The solution was concentrated under reduced pressure to afford a thick oil. The oil was poured into isopropanol (1 L) with vigorous stirring. The resulting suspension was collected on a sintered funnel while rinsing with cold isopropanol. The product was further dried under high vacuum overnight to afford 7.6 g as a light brown solid in 71% yield.

Example 4

Synthesis of 4-Aminosancycline

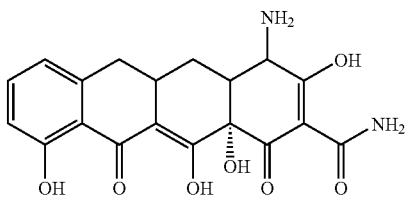

To a solution of 4-oximinosancycline, (11.1 g, 25.0 mmol) in methanol (250 mL) and acetic acid (7.22 mL, 125 mmol) was added 5% palladium on carbon. The solution was flushed with hydrogen and placed under vacuum for three successive cycles. After the final cycle, the flask was placed under 50 psi of hydrogen for 16 hours. After flushing the flask with nitrogen and placing it under vacuum for three successive cycles, the solution was filtered through a plug of celite, while rinsing with methanol. The solution was concentrated under reduced pressure to afford a thick oil. The oil was poured into isopropanol (1 L) with vigorous stirring. The resulting suspension was collected on a sintered funnel while rinsing with cold isopropanol. The product was further dried under high vacuum overnight to afford 7.6 g as a light brown solid in 71% yield.

Example 5

Synthesis of 4-Acylminocycline

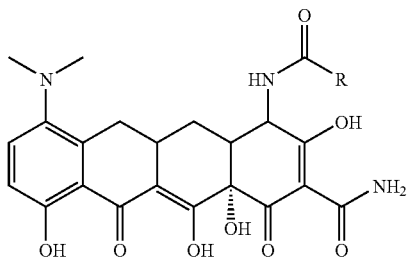

To a solution of 4-aminominocycline (502 mg, 1.00 mmol) in DMPU (2.5 mL) and acetonitrile (2.5 mL) at room temperature was added 1.5 eq. acylating reagent. After monitoring by HPLC, the reaction was judged complete after 3 hours. The solution was diluted with water (20 mL) and was run through a small plug of DVB resin eluting with a gradient (100 mL) of acetonitrile and water (5%-10%-20%-50%). The fraction containing the product was concentrated under reduced pressure and further dried under vacuum.

Example 6

Synthesis of 4-Acylsancycline

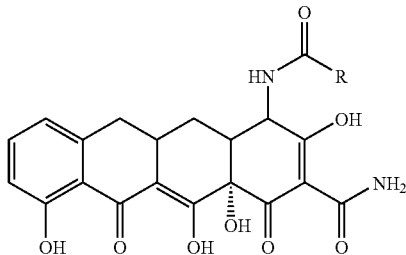

To a solution of 4-aminosancycline (502 mg, 1.00 mmol) in DMPU (2.5 mL) and acetonitrile (2.5 mL) at room temperature was added 1.5 eq. acylating reagent. After monitoring by HPLC, the reaction was judged complete after 3 hours. The solution was diluted with water (20 mL) and was run through a small plug of DVB resin eluting with a gradient (100 mL) of acetonitrile and water (5%-10%-20%-50%). The fraction containing the product was concentrated under reduced pressure and further dried under vacuum.

Example 7

Synthesis of 4-Dialkylminocycline

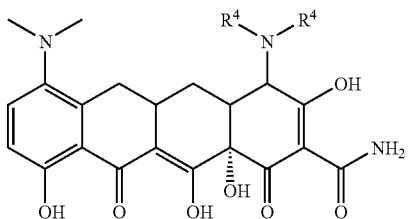

To a solution of 4-aminominocycline (502 mg, 1.00 mmol) and 5 eq. aldehyde in methanol (10 mL) and triethylamine (1 mL) was added 5% palladium on carbon (350 mg). The solution was flushed with hydrogen and placed under vacuum for three successive cycles. After the final cycle, the flask was placed under 20 psi of hydrogen for 12 hours. After flushing the flask with nitrogen and placing it under vacuum for three successive cycles, the solution was filtered through a plug of celite, while rinsing with methanol. The solution was concentrated under reduced pressure, diluted with 0.5M HCl (20 mL) and loaded onto a plug of DVB resin. The water solution was run through the plug of DVB resin eluting with a 100 mL gradient of acetonitrile and water (5%-10%-20%-50%). The fraction containing the product was concentrated under reduced pressure and further dried under vacuum.

Example 8

Synthesis of 4-Dialkylsancycline

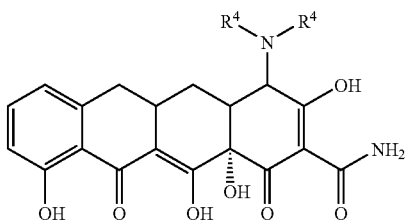

To a solution of 4-aminosancycline (502 mg, 1.00 mmol) and 5 eq. aldehyde in methanol (10 mL) and triethylamine (1 mL) was added 5% palladium on carbon (350 mg). The solution was flushed with hydrogen and placed under vacuum for three successive cycles. After the final cycle, the flask was placed under 20 psi of hydrogen for 12 hours. After flushing the flask with nitrogen and placing it under vacuum for three successive cycles, the solution was filtered through a plug of celite, while rinsing with methanol. The solution was concentrated under reduced pressure, diluted with 0.5M HCl (20 mL) and loaded onto a plug of DVB resin. The water solution was run through the plug of DVB resin eluting with a 100 mL gradient of acetonitrile and water (5%-10%-20%-50%). The fraction containing the product was concentrated under reduced pressure and further dried under vacuum.

Example 9

In Vitro Minimum Inhibitory Concentration (MIC) Assay

The following assay is used to determine the efficacy of tetracycline compounds against common bacteria. 2 mg of each compound is dissolved in 100 µl of DMSO. The solution is then added to cation-adjusted Mueller Hinton broth (CAMHB), which results in a final compound concentration of 200 µg per ml. The tetracycline compound solutions are diluted to 50 µL volumes, with a test compound concentration of 0.098 µg/ml. Optical density (OD) determinations are made from fresh log-phase broth cultures of the test strains. Dilutions are made to achieve a final cell density of $1 \times 10^6$ CFU/ml. At OD=1, cell densities for different genera should be approximately:

| | |
|---|---|
| E. coli | $1 \times 10^9$ CFU/ml |
| S. aureus | $5 \times 10^8$ CFU/ml |
| Enterococcus sp. | $2.5 \times 10^9$ CFU/ml |

50 µl of the cell suspensions are added to each well of microtiter plates. The final cell density should be approximately $5 \times 10^5$ CFU/ml. These plates are incubated at 35° C. in an ambient air incubator for approximately 18 hr. The plates are read with a microplate reader and are visually inspected when necessary. The MIC is defined as the lowest concentration of the tetracycline compound that inhibits growth.

EQUIVALENTS

Those skilled in the art will recognize, or be able to ascertain using no more than routine experimentation, numerous equivalents to the specific procedures described herein. Such equivalents are considered to be within the scope of the present invention and are covered by the following claims. The contents of all references, patents, and patent applications cited throughout this application are hereby incorporated by reference. The appropriate components, processes, and methods of those patents, applications and other documents may be selected for the present invention and embodiments thereof.

The invention claimed is:

1. A compound of formula (I):

wherein:
$R^{2'}$ and $R^2$ are each independently hydrogen, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^{10}$, $R^{11}$ and $R^{12}$ are each independently hydrogen, alkyl, aryl, benzyl, arylalkyl, or a prodrug moiety;
$R^3$ is hydrogen, or a prodrug moiety;
$R^4$ is N—$OR^{4a}$;
$R^{4a}$ is hydrogen, alkyl, alkenyl, alkynyl, or aryl;
$R^5$ and $R^{5'}$ are each independently hydroxyl, hydrogen, thiol, alkanoyl, aroyl, alkaroyl, aryl, heteroaromatic, alkyl, alkenyl, alkynyl, alkoxy, alkylthio, alkylsulfinyl, alkylsulfonyl, alkylamino, arylalkyl, alkyl carbonyloxy, or aryl carbonyloxy;
$R^6$ and $R^{6'}$ are each independently hydrogen, methylene, halogen, thiol, alkyl, alkenyl, alkynyl, aryl, alkylthio, alkylsulfinyl, alkylsulfonyl, alkylamino, or an arylalkyl;
$R^7$ is hydrogen or dimethylamino;
$R^8$ is hydrogen, hydroxyl, halogen, thiol, nitro, alkyl, alkenyl, alkynyl, aryl, alkoxy, alkylthio, alkylsulfinyl, alkylsulfonyl, alkylamino, amino, arylalkenyl, arylalkynyl, acyl, aminoalkyl, heterocyclic, thionitroso, or —$(CH_2)_{0-3}(NR^{8c})_{0-1}C(=E')ER^{8a}$;
$R^9$ is hydrogen or aminoalkyl;
$R^{8a}$, $R^{8b}$, $R^{8c}$, $R^{8d}$, $R^{8e}$ and $R^{8f}$ are each independently hydrogen, acyl, alkyl, alkenyl, alkynyl, alkoxy, alkylthio, alkylsulfinyl, alkylsulfonyl, alkylamino, arylalkyl, aryl, heterocyclic, heteroaromatic or a prodrug moiety;
$R^{13}$ is hydrogen, hydroxyl, alkyl, alkenyl, alkynyl, alkoxy, alkylthio, aryl, alkylsulfinyl, alkylsulfonyl, alkylamino, or an arylalkyl;
E is $CR^{8d}R^{8e}$, S, $NR^{8b}$ or O;
E' is O, $NR^{8f}$, or S;
X is $CHC(R^{13}Y'Y)$, $C=CR^{13}Y$, $CR^{6'}R^6$, S, $NR^6$, O;
Y' and Y are each independently hydrogen, halogen, hydroxyl, cyan, sulfhydryl, amino, alkyl, alkenyl, alkynyl, alkoxy, alkylthio, alkylsulfinyl, alkylsulfonyl, alkylamino, or an arylalkyl; or a pharmaceutically acceptable salt, ester or enantiomer thereof.

2. The compound of claim 1, wherein $R^{2'}$, $R^3$, $R^{10}$, $R^{11}$, and $R^{12}$ are each hydrogen or a prodrug moiety; X is $CR^{6'}R^6$; and $R^2$, $R^5$, $R^{5'}$, $R^6$, and $R^{6'}$ are each hydrogen.

3. The compound of claim 1, wherein X is $CR^{6'}R^6$; $R^5$, $R^{5'}$, $R^6$ and $R^{6'}$ are each hydrogen and $R^7$ is dimethylamino.

4. The compound of claim 2, wherein $R^9$ is hydrogen.

5. The compound of claim 2, wherein $R^7$ is dimethylamino.

6. The compound of claim 2, wherein $R^8$ is hydrogen.

7. The compound of claim 2, wherein $R^4$ is N—OH.

8. The compound of claim 1, wherein said compound is selected from the group consisting of:

-continued
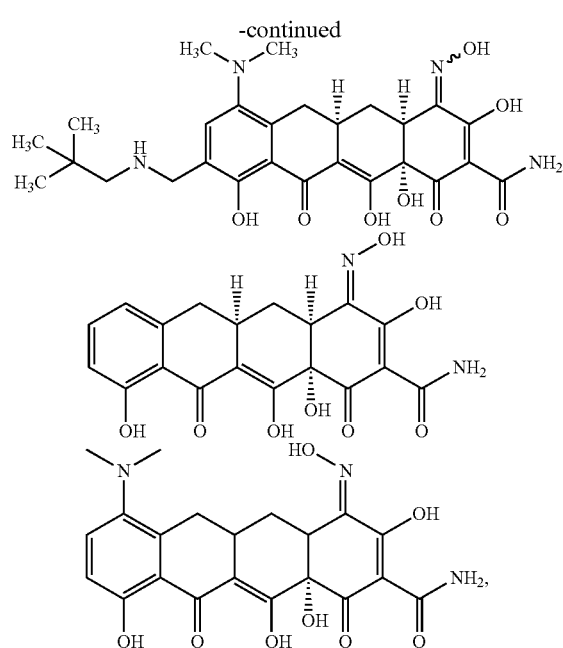
9. A compound selected from:
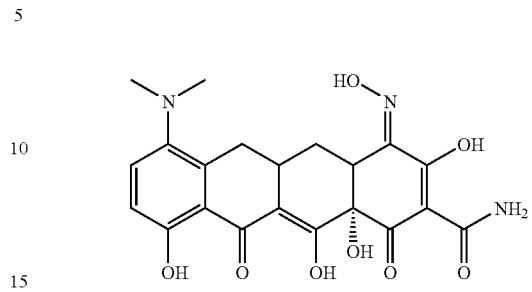
and pharmaceutically acceptable salts, esters and enantiomers thereof.
10. A pharmaceutical composition comprising a therapeutically effective amount of a compound of claim 1 and a pharmaceutically acceptable carrier.
* * * * *

UNITED STATES PATENT AND TRADEMARK OFFICE
CERTIFICATE OF CORRECTION

| | | |
|---|---|---|
| PATENT NO. | : 7,858,601 B2 | Page 1 of 1 |
| APPLICATION NO. | : 11/258613 | |
| DATED | : December 28, 2010 | |
| INVENTOR(S) | : Joel Berniac et al. | |

It is certified that error appears in the above-identified patent and that said Letters Patent is hereby corrected as shown below:

In claim 1, at column 44, line 11, "$R^7$ is hydrogen or dimethylamino" should read --$R^7$ is hydrogen, aryl, or dimethylamino--.

In claim 1, at column 44, line 30, "hydroxyl, cyan, sulfhydryl" should read --hydroxyl, cyano, sulfhydryl--.

Signed and Sealed this
Eleventh Day of September, 2012

David J. Kappos
*Director of the United States Patent and Trademark Office*